(12) United States Patent
Eyckerman et al.

(10) Patent No.: US 8,003,757 B2
(45) Date of Patent: *Aug. 23, 2011

(54) RECEPTOR-BASED INTERACTION TRAP

(75) Inventors: Sven Eyckerman, Brasschaat (BE); Xaveer van Ostade, Lokeren (BE); Joel S. Vandekerckhove, Loppem (BE); Annick Verhee, Lichtervelde (BE); Jan Tavernier, Balegem (BE)

(73) Assignee: Vlaams Interuniversitair Instituut Voor Biotechnologie VZW, Gent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/653,484

(22) Filed: Dec. 14, 2009

(65) Prior Publication Data

US 2010/0173408 A1  Jul. 8, 2010

Related U.S. Application Data

(63) Continuation of application No. 10/303,157, filed on Nov. 22, 2002, now Pat. No. 7,855,270, which is a continuation of application No. PCT/EP01/05916, filed on May 22, 2001.

(30) Foreign Application Priority Data

May 22, 2000 (EP) .................................. 00201771

(51) Int. Cl.
*C07K 19/00* (2006.01)
*C12N 5/10* (2006.01)
*C12N 1/15* (2006.01)
*G01N 33/566* (2006.01)

(52) U.S. Cl. .... 530/350; 435/7.2; 435/325; 435/254.11; 435/419

(58) Field of Classification Search .................... None
See application file for complete search history.

(56) References Cited

U.S. PATENT DOCUMENTS

| | | |
|---|---|---|
| 5,521,066 A | 5/1996 | Menzel et al. |
| 5,686,281 A | 11/1997 | Roberts |
| 5,716,622 A | 2/1998 | Darnell et al. |
| 5,744,314 A | 4/1998 | Menzel et al. |
| 5,776,689 A | 7/1998 | Karin et al. |
| 5,843,697 A | 12/1998 | Pestka et al. |
| 5,885,779 A | 3/1999 | Sadowski et al. |
| 5,935,797 A | 8/1999 | Clayberger et al. |
| 5,972,621 A | 10/1999 | Tartaglia et al. |
| 6,001,816 A | 12/1999 | Morsy et al. |
| 6,270,964 B1 | 8/2001 | Michnick et al. |

(Continued)

FOREIGN PATENT DOCUMENTS

EP   0 646 644 A2   4/1995

(Continued)

OTHER PUBLICATIONS

Banks et al., Activiation of Downstream Signals by the Long Form of the Leptin Receptor, Journal of Biological Chemistry, May 12. 2000, pp. 14563-14572, vol. 275. No. 19, U.S.A.

(Continued)

*Primary Examiner* — Bridget E Bunner
*Assistant Examiner* — Zachary Howard
(74) *Attorney, Agent, or Firm* — TraskBritt, P.C.

(57) ABSTRACT

Described is a recombinant receptor comprising an extracellular ligand-binding domain and a cytoplasmic domain that comprises a heterologous bait polypeptide. The recombinant receptor is activated by binding of a ligand to the ligand-binding domain and by binding of a prey polypeptide to the heterologous bait peptide. The invention also discloses a method for detecting compound-compound binding using the recombinant receptor.

5 Claims, 14 Drawing Sheets

U.S. PATENT DOCUMENTS

| | | |
|---|---|---|
| 6,294,330 B1 | 9/2001 | Michnick et al. |
| 6,303,319 B1 | 10/2001 | Rickles |
| 6,342,345 B1 | 1/2002 | Blau et al. |
| 6,734,006 B2 | 5/2004 | Xiao et al. |
| 7,575,878 B2 | 8/2009 | Tavernier et al. |
| 2001/0023062 A1 | 9/2001 | Ostade et al. |

FOREIGN PATENT DOCUMENTS

| | | |
|---|---|---|
| WO | WO 97/00319 | 1/1997 |
| WO | WO 97/20933 | 6/1997 |
| WO | WO97/26335 | 7/1997 |
| WO | WO 97/31113 | 8/1997 |
| WO | WO 97/46585 | 12/1997 |
| WO | WO 98/02542 | 1/1998 |
| WO | WO 98/12224 | 3/1998 |
| WO | WO 98/20158 | 5/1998 |
| WO | WO 98/34120 | 8/1998 |
| WO | WO 98/44350 | 10/1998 |
| WO | WO 99/03974 | 1/1999 |
| WO | WO 99/40946 A2 | 8/1999 |
| WO | WO 00/06722 | 2/2000 |
| WO | WO 00 07014 | 2/2000 |
| WO | WO 00/07038 | 2/2000 |
| WO | WO 02/40543 A1 | 5/2002 |
| WO | WO 02/062833 A2 | 8/2002 |

OTHER PUBLICATIONS

Bannasch et al., Oncogene, 1999, pp. 6810-6817. vol. 18.

Bao et al., Oncogene, 1996, pp. 2171-2176, vol. 12.

Baumann et al., Proc. Natl. Acad. Sci. USA, 1996, pp. 8374-8378, vol. 93.

Beattie et al., Obesity and Hyperleptinemia in Metallothionein (-I and -II) Null Mice. Proceedings of the National Academy of Sciences of USA, Jan. 1998, pp. 358-363, vol. 95.

Bjorbaek et al., Identification of SOCS-3 as a Potential Mediator of Central Leptin Resistance, Molecular Cell, Mar. 1998, pp. 619-625, vol. 1, No. 4.

Bjorbaek et al., The Role of SOCS-3 in Leptin Signaling and Leptin Resistance, The Journal of Biological Chemistry, Oct. 15, 1999, pp. 30059-30065, vol. 274, No. 42.

Bonnefoy-Berard et al., "Vav: Function and Regulation in Hematopoietic Cell Signaling." 14 Stem Cells 250-68 (1996).

Campfield et al., Science. 1998, pp. 1383-1389, vol. 280.

Carpenter et al., Proc. Natl Acad Sci USA. 1998. pp. 6061-6066, vol. 95.

Colas et al., The impact of two-hybrid and related methods on biotechnology, Trends in Biotechnology, Aug. 1998, pp. 355-363, vol. 16.

Daly et al., Recognition of human colon cancer by T cells transduced with a chimeric receptor gene, Cancer Gene Therapy, 2000, pp. 284-291, vol. 7, No. 2.

David et al., J. Biol. Chem. 1996, pp. 4585-4588, vol. 271.

Dusetti et al., Abstract, Structural organization of the gene encoding the rat pancreatitis-associated protein, Jul. 5, 1993, pp. 14470-14475, vol. 268.

Dusetti et al., The pancreatitis-associated protein I promoter allows targeting to the pancreas of a foreign gene whose expression is up-regulated during pancreatic inflammation, Feb. 28, 1997, pp. 5800-5804.

Estojak et al., 1995, Molecular and Cellular Biology, pp. 5820-5829, vol. 15, No. 10.

Eyckerman et al., Analysis of Tyr to Phe and fa/fa leptin receptor mutations in the PC12 cell line, Eur. Cytokine Netw, Dec. 1999. pp. 549-556, vol. 10. No. 4.

Eyckerman et al., Design and application of a cytokine-receptor-based interaction trap, Nature Cell Biology. Dec. 2001, pp. 1114-1119, vol. 3.

Fields et al., The two-hybrid system: an assay for protein-protein interactions, Trends in Genetics, Aug. 1994, pp. 286-292, vol. 10, No. 8.

Fujiwara et al., Biochemistry, 2002, pp. 12729-12738, vol. 1, No. 42.

Ghilardi et al., Proc. Natl. Acad. Sci. USA, 1996, pp. 6231-6235, vol. 93.

Gisselbrecht, Sylvie, The CIS/SOCS proteins: a family of cytokine-inducible regulators of signaling. 10(4) European Cytokine Network 463-470 (Dec. 1999). retrieved from <URL:http://www.john-libbey-eurotest.fr/articles/ccn/10/4/463-70/> Jul. 12, 2001.

Grasso et al., Endocrinol. 1997, pp. 1413-1418, vol. 138.

Hertveldt et al., Identification of Ga180p-interacting proteins by *Saccharomyces cerevisiae* while genome phage display, Gene, 2003, pp. 141-149, vol. 307.

Hilpert et al., Protein Engineering, 2001, pp. 803-806 (11 pages as printed) vol. 14, No. 10.

Ihle et al., Abstract. Jaks and Stats in signaling by the cytokine receptor superfamily, Trends Genet., Feb. 1995, pp. 69-74, vol. 11, No. 2.

Iyengar, FASEB J., 1993, pp. 768-775, vol. 7.

Junqueira et al., Oncogene, 2003, pp. 2772-2781, vol. 22.

Lee et al., Abnormal splicing of the leptin receptor in diabetic mice, Nature, Feb. 15, 1996, pp. 632-635, vol. 379.

Medici et al., The EMBO Journal, 1997, pp. 7241-7249, vol. 16, No. 24.

Mercer et al., Localization of leptin receptor mRNA and the long form splice variant (Ob-Rb) in mouse hypothalamus and adjacent brain regions by in situ hybridization, FEBS Letters, 1996, pp. 113-116, vol. 387.

Montoye et al., Analysis of leptin signalling in hematopoietic cells using an adapted MAPPIT strategy, FEBS Letters, 2006, pp. 3301-3307, vol. 580.

Montoye et al., Blood, 2005, pp. 4264-4271, vol. 11, No. 105.

Montoye et al., In Press. A systematic scan of interactions with tyrosine motifs in the erythropoietin receptor using a mammalian two-hybrid approach.

Murray et al., Journal of Immunology, 2007, pp. 2623-2629, vol. 5.

Nakashima et al., FEBS, 1997, pp. 79-82, vol. 403.

Ngo et al., The Protein Folding Problem and Tertiary Structure Prediction, Chapter 14: Computational Complexity Protein Structure Prediction, and the Levinthal Paradox. Mar. 2, 1994, pp. 492-495.

Okuda et al., Ann N Y Acad Sci., 1999, pp. 305-312, vol. 872.

Osborne et al., The Yeats Tribrid System—Genetic Detection of trans-phosphorylated ITAM-SH2-Interactions. Biotechnology, Dec. 13, 1995, pp. 1474-1478, vol. 13.

Overton et al., Current Biology, 2000, pp. 341-344, vol. 10, No. 6.

PCT International Search Report, PCT/EP01/05916, dated Apr. 18, 2002, 3 pages.

Ray et al., J. Clin. Invest. 1996, pp. 1852-1859, vol. 97.

Record for GenBank Accession NM_14616, *Mus musculus* leptin receptor (Lepr), transcript variant 1. mRNA. printed Jan. 16, 2008.

Rohner-Jearnrenaud et al., The New Eng. J. Med., 1996, pp. 324-325, vol. 334.

Saitoh et al., Identification of Important Regions in the Cytoplasmic Justamembrane Domain of Type I Receptor That Separate Signaling Pathways of Transforming Growth Factor-beta. The Journal of Biological Chemistry, Feb. 2, 1996. pp. 2769-2775, vol. 271, No. 5.

Shores et al., Curr Opin Immunol., 1997, pp. 380-389, vol. 9, No. 3.

Stoffel et al., Permissive role of thrombopoietin and granulocyte colony-stimulating factor receptors in hematopoietic cell fate decision in vivo, Proc. Natl. Acad. Sci. Jan. 1999, pp. 698-702, vol. 96.

Tartaglia et al., Identification and Expression Cloning of a Leptin Receptor. OB-R, Cell. Dec. 29, 1995. pp. 1263-1271, vol. 83.

Vaisse et al., Leptin Activation of Stat3 in the Hypothalamus of Wild-Type and ob/ob Mice but not db/db Mice. Nature Genetics, Sep. 14, 1996, pp. 95-97, vol. 14.

Van Criekinge et al., Yeast Two-Hybrid: State of the Art, Biological Procedures Online, Oct. 4, 1999, vol. 2, No. 1, <www.biologicalprocedures.com>.

Wells, Additivity of Mutational Effects in Proteins, Biochemistry, Sep. 18, 1990, pp. 8509-8517, vol. 29, No. 37.

Zabeau et al., The ins and outs of leptin receptor activation, FEBS Letters, 2003, pp. 45-50, vol. 546.

Zhang et al., Nature Biotechnology, 2000, pp. 71-74. vol. 18.

Office Action for U.S. Appl. No. 10/303,157, dated Feb. 8, 2005.

Office Action for U.S. Appl. No. 10/303,157, dated Jul. 29, 2005.

Office Action for U.S. Appl. No. 10/303,157, dated Jul. 7, 2006.

Office Action for U.S. Appl. No. 10/303,157, dated Jan. 16, 2007.

Office Action for U.S. Appl. No. 10/303,157, dated Aug. 8, 2007.

Office Action for U.S. Appl. No. 10/303,157, dated Jan. 28, 2008.

Office Action for U.S. Appl. No. 10/303,157, dated Feb. 5, 2009.

Office Action for U.S. Appl. No. 10/303,157, dated Oct. 14, 2009.

U.S. Appl. No. 10/303,157, filed Nov. 22, 2002, Inventor : Eyckerman et al., Title : Receptor-Based Interaction Trap.

U.S. Appl. No. 10/751,072, filed Jan. 2, 2004, Inventor: Eykerman et al., Title: Reversed Mammalian Protein-Protein Interaction Trap.

U.S. Appl. No. 12/459,278, filed Jun. 29, 2009, Inventor: Kas et al., Title: Peptide Combos and Their Uses.

U.S. Appl. No. 11/305,737, filed Dec. 16, 2005, Inventor: Kas et al., Title: Peptide Combos and Their Uses.

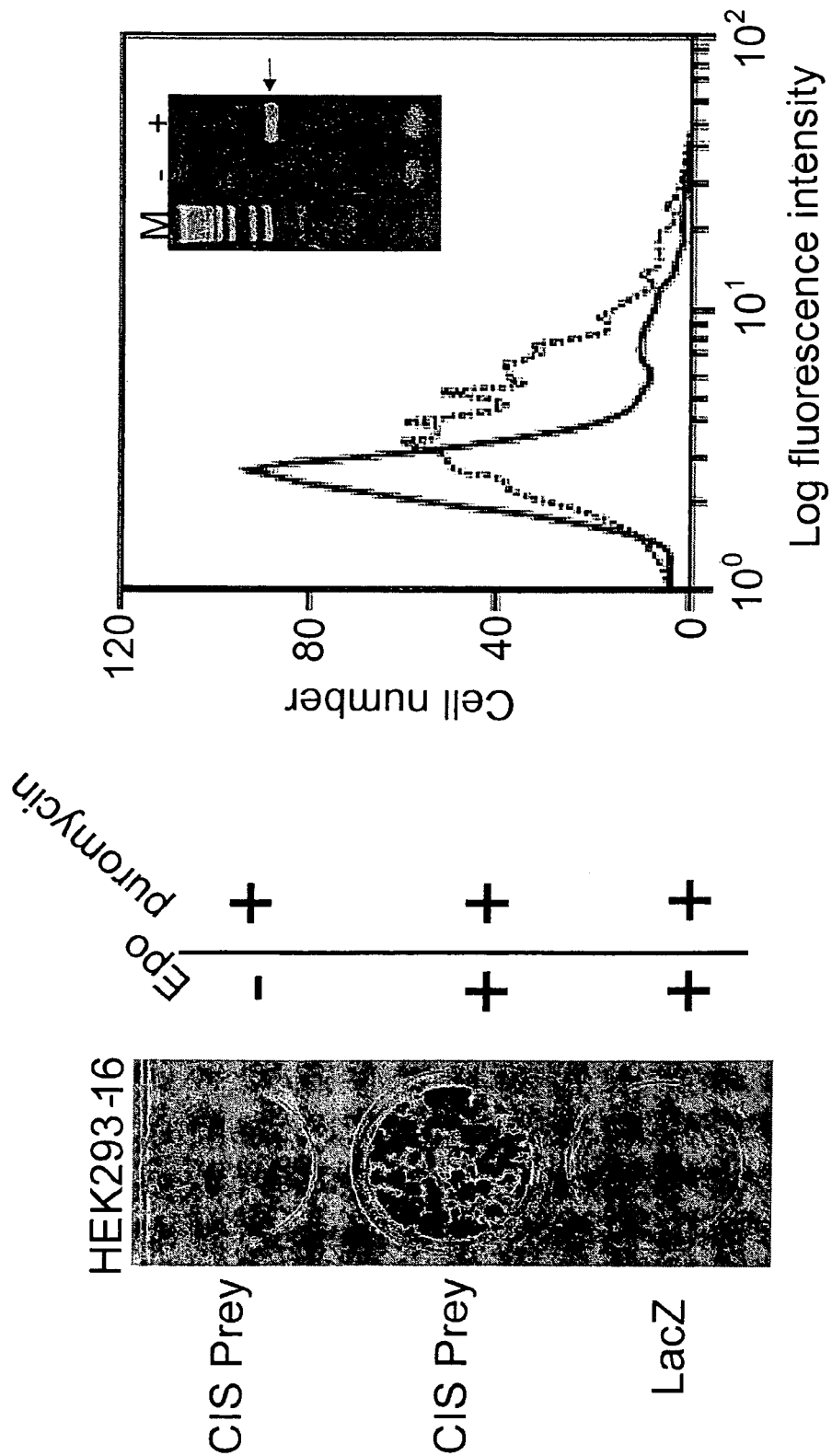

SEQUENCE LISTING

```
<160> NUMBER OF SEQ ID NOS: 53

<210> SEQ ID NO 1
<211> LENGTH: 41
<212> TYPE: DNA
<213> ORGANISM: Artificial Sequence
<220> FEATURE:
<223> OTHER INFORMATION: synthesized sequence, forward primer:
      MBU-O-157; Y985F mutagenesis in mLepR

<400> SEQUENCE: 1
gagacaaccc tcagttaaat ttgcaactct ggtcagcaac g                41

<210> SEQ ID NO 2
<211> LENGTH: 41
<212> TYPE: DNA
<213> ORGANISM: Artificial Sequence
<220> FEATURE:
<223> OTHER INFORMATION: synthesized sequence, reverse primer:
      MBU-O-158; Y985F mutagenesis in mLepR

<400> SEQUENCE: 2
cgttgctgac cagagttgca aatttaactg agggttgtct c                41

<210> SEQ ID NO 3
<211> LENGTH: 41
<212> TYPE: DNA
<213> ORGANISM: Artificial Sequence
<220> FEATURE:
<223> OTHER INFORMATION: synthesized sequence, forward primer:
      MBU-O-159; Y1077F mutagenesis in mLepR

<400> SEQUENCE: 3
gggagaagtc tgtctgtttt ctaggggtca cctccgtcaa c                41

<210> SEQ ID NO 4
<211> LENGTH: 41
<212> TYPE: DNA
<213> ORGANISM: Artificial Sequence
<220> FEATURE:
<223> OTHER INFORMATION: synthesized sequence, reverse primer:
      MBU-O-160; Y1077F mutagenesis in mLepR

<400> SEQUENCE: 4
gttgacggag gtgacccta gaaaacagac agacttctcc c                41

<210> SEQ ID NO 5
<211> LENGTH: 43
<212> TYPE: DNA
<213> ORGANISM: Artificial Sequence
<220> FEATURE:
<223> OTHER INFORMATION: synthesized sequence, forward primer:
      MBU-O-161; Y1138F mutagenesis in mLepR
```

<400> SEQUENCE: 5
ctggtgagaa ctttgtacct tttatgcccc aatttcaaac ctg                43

<210> SEQ ID NO 6
<211> LENGTH: 43
<212> TYPE: DNA
<213> ORGANISM: Artificial Sequence
<220> FEATURE:
<223> OTHER INFORMATION: synthesized sequence, reverse primer:
      MBU-O-162: Y1138F mutagenesis in mLepR

<400> SEQUENCE: 6
caggtttgaa attggggcat aaaaggtaca aagttctcac cag                43

<210> SEQ ID NO 7
<211> LENGTH: 30
<212> TYPE: DNA
<213> ORGANISM: Artificial Sequence
<220> FEATURE:
<223> OTHER INFORMATION: synthesized sequence, forward primer:
      MBU-O-167; hEpoR primer

<400> SEQUENCE: 7
cggggtacca tggaccacct cggggcgtcc                30

<210> SEQ ID NO 8
<211> LENGTH: 22
<212> TYPE: DNA
<213> ORGANISM: Artificial Sequence
<220> FEATURE:
<223> OTHER INFORMATION: synthesized sequence, forward primer:
      MBU-O-222; rPAP1 promoter primer

<400> SEQUENCE: 8
ctgcagattt tccagttagt ca                22

<210> SEQ ID NO 9
<211> LENGTH: 20
<212> TYPE: DNA
<213> ORGANISM: Artificial Sequence
<220> FEATURE:
<223> OTHER INFORMATION: synthesized sequence, reverse primer:
      MBU-O-223; rPAP1 promoter primer

<400> SEQUENCE: 9
tggatggttt gtgaggacag                20

<210> SEQ ID NO 10
<211> LENGTH: 32
<212> TYPE: DNA
<213> ORGANISM: Artificial Sequence
<220> FEATURE:
<223> OTHER INFORMATION: synthesized sequence, reverse primer:
      MBU-O-308; hEpoR primer

<400> SEQUENCE: 10
cccttaatta agtccaggtc gctaggcgtc ag                32

<210> SEQ ID NO 11
<211> LENGTH: 35
<212> TYPE: DNA
<213> ORGANISM: Artificial Sequence
<220> FEATURE:
<223> OTHER INFORMATION: synthesized sequence, reverse primer:
      MBU-O-443; hgp130 primer

<400> SEQUENCE: 11

```
gcgaattccg aaccgccctg aggcatgtag ccgcc                               35
```

<210> SEQ ID NO 12
<211> LENGTH: 32
<212> TYPE: DNA
<213> ORGANISM: Artificial Sequence
<220> FEATURE:
<223> OTHER INFORMATION: synthesized sequence, forward primer:
      MBU-O-445; SV40LargeT primer

<400> SEQUENCE: 12

```
gcgaattcga agcagaggaa actaaacaag tg                                  32
```

<210> SEQ ID NO 13
<211> LENGTH: 55
<212> TYPE: DNA
<213> ORGANISM: Artificial Sequence
<220> FEATURE:
<223> OTHER INFORMATION: synthesized sequence, reverse primer:
      MBU-O-446; SV40LargeT primer

<400> SEQUENCE: 13

```
cgtctagagc ggccgcagat ctcgagtcgc gattatgttt caggttcagg gggag         55
```

<210> SEQ ID NO 14
<211> LENGTH: 31
<212> TYPE: DNA
<213> ORGANISM: Artificial Sequence
<220> FEATURE:
<223> OTHER INFORMATION: synthesized sequence, forward primer:
      MBU-O-447; mLepR intracellular and transmembrane fragment

<400> SEQUENCE: 14

```
gcttaattaa cgggctgtat gtcattgtac c                                   31
```

<210> SEQ ID NO 15
<211> LENGTH: 63
<212> TYPE: DNA
<213> ORGANISM: Artificial Sequence
<220> FEATURE:
<223> OTHER INFORMATION: synthesized sequence, reverse primer:
      MBU-O-448; mLepR intracellular and transmembrane fragment

<400> SEQUENCE: 15

```
cgtctagatt agcggccgct tactagtgag ctcgtcgacc cacccacagt taagtcacac    60
atc                                                                  63
```

<210> SEQ ID NO 16
<211> LENGTH: 27
<212> TYPE: DNA
<213> ORGANISM: Artificial Sequence
<220> FEATURE:
<223> OTHER INFORMATION: synthesized sequence, forward primer:
      MBU-O-450; mp53 primer

<400> SEQUENCE: 16

```
gtgtcgacgg tcaccgagac ccctggg                                        27
```

<210> SEQ ID NO 17
<211> LENGTH: 28
<212> TYPE: DNA
<213> ORGANISM: Artificial Sequence
<220> FEATURE:
<223> OTHER INFORMATION: synthesized sequence, reverse primer:
      MBU-O-451; mp53 primer

<400> SEQUENCE: 17

```
gctctagatc attgcggggg agaggcgc                                               28
```

<210> SEQ ID NO 18
<211> LENGTH: 27
<212> TYPE: DNA
<213> ORGANISM: Artificial Sequence
<220> FEATURE:
<223> OTHER INFORMATION: synthesized sequence, forward primer:
      MBU-O-467; hGRB2 primer

<400> SEQUENCE: 18

```
ggaattcatg gaagccatcg ccaaata                                                27
```

<210> SEQ ID NO 19
<211> LENGTH: 28
<212> TYPE: DNA
<213> ORGANISM: Artificial Sequence
<220> FEATURE:
<223> OTHER INFORMATION: synthesized sequence, reverse primer:
      MBU-O-468; hGRB2 primer

<400> SEQUENCE: 19

```
gctctagatt agacgttccg gttcacgg                                               28
```

<210> SEQ ID NO 20
<211> LENGTH: 27
<212> TYPE: DNA
<213> ORGANISM: Artificial Sequence
<220> FEATURE:
<223> OTHER INFORMATION: synthesized sequence, forward primer:
      MBU-O-469; hGRB2 SH2 primer

<400> SEQUENCE: 20

```
ggaattctgg tttttggca aaatccc                                                 27
```

<210> SEQ ID NO 21
<211> LENGTH: 28
<212> TYPE: DNA
<213> ORGANISM: Artificial Sequence
<220> FEATURE:
<223> OTHER INFORMATION: synthesized sequence, reverse primer:
      MBU-O-470; hGRB2 SH2 primer

<400> SEQUENCE: 21

```
gctctagatt acggctgctg tggcacct                                               28
```

<210> SEQ ID NO 22
<211> LENGTH: 59
<212> TYPE: DNA
<213> ORGANISM: Artificial Sequence
<220> FEATURE:
<223> OTHER INFORMATION: synthesized sequence, forward primer:
      MBU-O-515; mutagenesis IRS1 primer

<400> SEQUENCE: 22

```
ggtgagaact ttgtaagccc gggtgaatat gtcaatattg aattccaatt tcaaacctg            59
```

<210> SEQ ID NO 23
<211> LENGTH: 59
<212> TYPE: DNA
<213> ORGANISM: Artificial Sequence
<220> FEATURE:
<223> OTHER INFORMATION: synthesized sequence, reverse primer:
      MBU-O-516; mutagenesis IRS1 primer

<400> SEQUENCE: 23

```
caggtttgaa attggaattc aatattgaca tattcacccg ggcttacaaa gttctcacc            59
```

<210> SEQ ID NO 24
<211> LENGTH: 38
<212> TYPE: DNA
<213> ORGANISM: Artificial Sequence
<220> FEATURE:
<223> OTHER INFORMATION: synthesized sequence, forward primer: MBU-O-567; mutagenesis ApaI site primer

<400> SEQUENCE: 24
gctctaaaag ctgcgggccc agtaggaatt ctaatacg        38

<210> SEQ ID NO 25
<211> LENGTH: 38
<212> TYPE: DNA
<213> ORGANISM: Artificial Sequence
<220> FEATURE:
<223> OTHER INFORMATION: synthesized sequence, reverse primer: MBU-O-568; mutagenesis ApaI site primer

<400> SEQUENCE: 25
cgtattagaa ttcctactgg gcccgcagct tttagagc        38

<210> SEQ ID NO 26
<211> LENGTH: 66
<212> TYPE: DNA
<213> ORGANISM: Artificial Sequence
<220> FEATURE:
<223> OTHER INFORMATION: synthesized sequence, forward primer: hgp130 primer

<400> SEQUENCE: 26
gacgggcccg ccaccatgga ttacaaggat gacgacgata agatctcgac cgtggtacac        60
agtggc        66

<210> SEQ ID NO 27
<211> LENGTH: 29
<212> TYPE: DNA
<213> ORGANISM: Artificial Sequence
<220> FEATURE:
<223> OTHER INFORMATION: synthesized sequence, forward primer: MBU-O-675; hEpoR intr fragment primer

<400> SEQUENCE: 27
ggcgagctcg gtgctggaca aatggttgc        29

<210> SEQ ID NO 28
<211> LENGTH: 32
<212> TYPE: DNA
<213> ORGANISM: Artificial Sequence
<220> FEATURE:
<223> OTHER INFORMATION: synthesized sequence, reverse primer: MBU-O-676; hEpoR intr. fragment primer

<400> SEQUENCE: 28
cgctctagat tactttaggt ggggtggggt ag        32

<210> SEQ ID NO 29
<211> LENGTH: 29
<212> TYPE: DNA
<213> ORGANISM: Artificial Sequence
<220> FEATURE:
<223> OTHER INFORMATION: synthesized sequence, forward primer: MBU-O-677; mCIS primer

<400> SEQUENCE: 29
gcggaattcg tcctctgcgt acagggatc        29

<210> SEQ ID NO 30
<211> LENGTH: 30
<212> TYPE: DNA
<213> ORGANISM: Artificial Sequence
<220> FEATURE:
<223> OTHER INFORMATION: synthesized sequence, reverse primer:
      MBU-O-678; mCIS primer

<400> SEQUENCE: 30
gcctctagat cagagttgga agggtactg                                  30

<210> SEQ ID NO 31
<211> LENGTH: 35
<212> TYPE: DNA
<213> ORGANISM: Artificial Sequence
<220> FEATURE:
<223> OTHER INFORMATION: synthesized sequence, forward primer:
      MBU-O-695; SV40LargeT primer

<400> SEQUENCE: 31
gcgagatctc ggaagcagag gaaactaaac aactg                           35

<210> SEQ ID NO 32
<211> LENGTH: 32
<212> TYPE: DNA
<213> ORGANISM: Artificial Sequence
<220> FEATURE:
<223> OTHER INFORMATION: synthesized sequence, reverse primer:
      MBU-O-696; SV40LargeT primer

<400> SEQUENCE: 32
gcgtctagat tatgtttcag gttcaggggg ag                              32

<210> SEQ ID NO 33
<211> LENGTH: 29
<212> TYPE: DNA
<213> ORGANISM: Artificial Sequence
<220> FEATURE:
<223> OTHER INFORMATION: synthesized sequence, forward primer:
      MBU-O-717; hEpoR Y426F mutagenesis

<400> SEQUENCE: 33
ctgccagctt tgaattcact atcctggac                                  29

<210> SEQ ID NO 34
<211> LENGTH: 29
<212> TYPE: DNA
<213> ORGANISM: Artificial Sequence
<220> FEATURE:
<223> OTHER INFORMATION: synthesized sequence, reverse primer:
      MBU-O-718; hEpoR Y426F mutagenesis

<400> SEQUENCE: 34
gtccaggata gtgaattcaa agctggcag                                  29

<210> SEQ ID NO 35
<211> LENGTH: 29
<212> TYPE: DNA
<213> ORGANISM: Artificial Sequence
<220> FEATURE:
<223> OTHER INFORMATION: synthesized sequence, forward primer:
      MBU-O-737; hVavS primer

<400> SEQUENCE: 35
gcggaattca agctggagga atgttctca                                  29

```
<210> SEQ ID NO 36
<211> LENGTH: 32
<212> TYPE: DNA
<213> ORGANISM: Artificial Sequence
<220> FEATURE:
<223> OTHER INFORMATION: synthesized sequence, reverse primer:
      MBU-O-738; hVavS primer

<400> SEQUENCE: 36
cgcctcgagt tacacgtagt tggcagggaa cc                              32

<210> SEQ ID NO 37
<211> LENGTH: 32
<212> TYPE: DNA
<213> ORGANISM: Artificial Sequence
<220> FEATURE:
<223> OTHER INFORMATION: synthesized sequence, reverse primer:
      MBU-O-741; hVavS primer

<400> SEQUENCE: 37
cgctctagat tacacgtagt tggcagggaa cc                              32

<210> SEQ ID NO 38
<211> LENGTH: 35
<212> TYPE: DNA
<213> ORGANISM: Artificial Sequence
<220> FEATURE:
<223> OTHER INFORMATION: synthesized sequence, forward primer:
      MBU-O-770; hGRB2 SH3 primer

<400> SEQUENCE: 38
gcgagatctc gacatacgtc caggccctct ttgac                           35

<210> SEQ ID NO 39
<211> LENGTH: 31
<212> TYPE: DNA
<213> ORGANISM: Artificial Sequence
<220> FEATURE:
<223> OTHER INFORMATION: synthesized sequence, forward primer:
      MBU-O-771; hVavS primer

<400> SEQUENCE: 39
gcgggatccc gaagctggag gaatgttctc a                               31

<210> SEQ ID NO 40
<211> LENGTH: 35
<212> TYPE: DNA
<213> ORGANISM: Artificial Sequence
<220> FEATURE:
<223> OTHER INFORMATION: synthesized sequence, forward primer:
      MBU-O-719; PuroR primer

<400> SEQUENCE: 40
ccgctcgagc caccatggcc gagtacaagc ccacg                           35

<210> SEQ ID NO 41
<211> LENGTH: 27
<212> TYPE: DNA
<213> ORGANISM: Artificial Sequence
<220> FEATURE:
<223> OTHER INFORMATION: synthesized sequence, reverse primer:
      MBU-O-720; PuroR primer

<400> SEQUENCE: 41
gctctagatt aggcaccggg cttgcgg                                    27

<210> SEQ ID NO 42
<211> LENGTH: 27
```

```
<212> TYPE: DNA
<213> ORGANISM: Artificial Sequence
<220> FEATURE:
<223> OTHER INFORMATION: synthesized sequence, forward primer:
      MBU-O-766; gp130 primer

<400> SEQUENCE: 42
gcgggatccg ccaccatgga ttacaag                                              27

<210> SEQ ID NO 43
<211> LENGTH: 33
<212> TYPE: DNA
<213> ORGANISM: Artificial Sequence
<220> FEATURE:
<223> OTHER INFORMATION: synthesized sequence, reverse primer:
      MBU-O-769; hEpoR primer

<400> SEQUENCE: 43
gcgcggccgc ttactttagg tggggtgggg tag                                       33

<210> SEQ ID NO 44
<211> LENGTH: 24
<212> TYPE: DNA
<213> ORGANISM: Artificial Sequence
<220> FEATURE:
<223> OTHER INFORMATION: synthesized sequence, forward primer:
      MBU-O-835; ccdB primer

<400> SEQUENCE: 44
cggaattcgc ttactaaaag ccag                                                 24

<210> SEQ ID NO 45
<211> LENGTH: 32
<212> TYPE: DNA
<213> ORGANISM: Artificial Sequence
<220> FEATURE:
<223> OTHER INFORMATION: synthesized sequence, reverse primer:
      MBU-O-836; ccdB primer

<400> SEQUENCE: 45
atagtttagc ggccgctaat tctatattcc cc                                        32

<210> SEQ ID NO 46
<211> LENGTH: 50
<212> TYPE: DNA
<213> ORGANISM: Artificial Sequence
<220> FEATURE:
<223> OTHER INFORMATION: synthesized sequence, forward primer: MBU-1094;
      Gateway primer

<400> SEQUENCE: 46
ccccaccact tgtacaaga aagctgggtc tgcattcatt ttatgtttca                      50

<210> SEQ ID NO 47
<211> LENGTH: 48
<212> TYPE: DNA
<213> ORGANISM: Artificial Sequence
<220> FEATURE:
<223> OTHER INFORMATION: synthesized sequence, reverse primer:
      MBU-O-1076; Gateway primer

<400> SEQUENCE: 47
ggggacaagt ttgtacaaaa aagcaggcta cttaccacag actgtacg                       48

<210> SEQ ID NO 48
<211> LENGTH: 10
<212> TYPE: PRT
<213> ORGANISM: Artificial Sequence
```

```
<220> FEATURE:
<223> OTHER INFORMATION: synthesized sequence, reverse flag-tag sequence
      encoded by primer MBU-O-586

<400> SEQUENCE: 48

Met Asp Tyr Lys Asp Asp Asp Asp Lys Ile
1               5                   10

<210> SEQ ID NO 49
<211> LENGTH: 9
<212> TYPE: PRT
<213> ORGANISM: Homo sapiens
<220> FEATURE:
<223> OTHER INFORMATION: phosphotyrosine encoding region from insulin
      receptor substrate 1 (IRS 1)

<400> SEQUENCE: 49

Pro Gly Glu Tyr Val Asn Ile Glu Phe
1               5

<210> SEQ ID NO 50
<211> LENGTH: 30
<212> TYPE: DNA
<213> ORGANISM: Artificial Sequence
<220> FEATURE:
<223> OTHER INFORMATION: synthesized sequence, biotinylated
      oligonucleotide direct against gp 130 chain

<400> SEQUENCE: 50
gggctgggta gactcggatc ttgagaagac                                    30

<210> SEQ ID NO 51
<211> LENGTH: 19
<212> TYPE: DNA
<213> ORGANISM: Artificial Sequence
<220> FEATURE:
<223> OTHER INFORMATION: synthesized sequence, primer used for RT-PCR of
      "prey" fragment

<400> SEQUENCE: 51
ggcatggagg ctgcgactg                                                19

<210> SEQ ID NO 52
<211> LENGTH: 20
<212> TYPE: DNA
<213> ORGANISM: Artificial Sequence
<220> FEATURE:
<223> OTHER INFORMATION: synthesized sequence, primer used for RT-PCR of
      "prey" fragment

<400> SEQUENCE: 52
tcgtcgacca ctgtgctggc                                               20

<210> SEQ ID NO 53
<211> LENGTH: 66
<212> TYPE: DNA
<213> ORGANISM: Artificial Sequence
<220> FEATURE:
<223> OTHER INFORMATION: synthesized sequence, MBU-O-586, hgp 130 primer
      for PCR amplification

<400> SEQUENCE: 53
gacgggcccg ccaccatgga ttacaaggat gacgacgata agatctcgac cgtggtacac   60
agtggc                                                              66
```

RECEPTOR-BASED INTERACTION TRAP

CROSS-REFERENCE TO RELATED APPLICATIONS

This application is a continuation of U.S. patent application Ser. No. 10/303,157, filed Nov. 22, 2002, now U.S. Pat. No. 7,855,270, which application is a continuation of PCT/EP01/05916, filed May 22, 2001, designating the United States of America, corresponding to WO 01/90188 (published in English on Nov. 29, 2001), which itself claims priority under Article 8 of the Patent Cooperation Treaty to EP 00201771.3, filed May 22, 2000, the contents of the entirety of each of which are incorporated herein in their entirety.

TECHNICAL FIELD

The invention relates to a recombinant receptor comprising an extracellular ligand-binding domain and a cytoplasmic domain that includes a heterologous bait polypeptide. The recombinant receptor is activated by the binding of a ligand to the ligand-binding domain and by the binding of a prey polypeptide to the heterologous bait peptide. The invention also relates to a method of detecting compound-compound-binding using the recombinant receptor.

BACKGROUND

Protein-protein interactions are an essential key in all biological processes, from the replication and expression of genes to the morphogenesis of organisms. Protein-protein interactions govern, among other things, ligand-receptor interactions and signaling pathways. The protein-protein interactions are also important in the assembly of enzyme subunits, in the formation of biological supramolecular structures, such as ribosomes, filaments and virus particles, and in antigen-antibody interactions.

Several approaches have been developed in attempts to identify protein-protein interactions. Some of the first techniques included co-purification of proteins and co-immunoprecipitation. However, these techniques are tedious and do not allow high throughput screening. Moreover, these techniques require lysis which corrupts the normal cellular context. A major breakthrough in the study of protein-protein interactions was achieved with the introduction of genetic approaches. Of the various genetic approaches, yeast two-hybrid (Fields and Song, 1989) is the most important one.

U.S. Pat. No. 5,637,463 describes an improvement of the yeast two-hybrid system which may be used to screen for modification-dependent protein-protein interactions. However, this method relies on the co-expression of a modifying enzyme which may exert its activity in the cytoplasm of the host organism. In this manner, the modifying enzyme may modify enzymes other than the protein involved in the protein-protein interaction and may affect the viability of the host organism.

Although the yeast two-hybrid system has been widely used, it has several drawbacks. One drawback is that the fusion proteins need to be translocated to the nucleus, which may not be evident. Also, proteins with intrinsic transcription activation properties may result in false positives. Moreover, protein-protein interactions that are dependent on secondary modifications of the protein, such as phosphorylation, may not be easily detected. To overcome some of these problems, alternative protein-protein interaction systems have been developed.

One of these alternative systems is an approach based on phage display that avoids the nuclear translocation drawback. PCT International Publication WO 9002809 describes an approach where a binding protein can be displayed on the surface of a genetic package, such as a filamentous phage, and the gene encoding the binding protein is packaged inside the phage. Phages bearing the binding protein that recognizes the target molecule are isolated and amplified. Several improvements of the phage display approach have been proposed and are as described in PCT International Publications WO 9220791, WO 9710330 and WO 9732017.

However, the phage display approaches suffer from difficulties inherent in phage display methodology. For instance, the proteins need to be exposed at the phage surface where the proteins are exposed to an environment that may not be physiologically relevant for the in vivo interaction. Moreover, when a phage library is screened, a competition exists between the phages which results in a selection of the high affinity-binding proteins. Also, modification-dependent phage display systems have not been described.

U.S. Pat. No. 5,776,689 describes a protein recruitment system which detects protein-protein interactions by recruitment of a guanine nucleotide exchange factor (Sos) to a plasma membrane where Sos activates a Ras reporter molecule. Activation of the Ras reporter molecule results in the survival of the cell that otherwise would not survive in the conditions used to culture the cell. Although this method allows the protein-protein interaction to take place under physiological conditions in the submembranary space, it has several drawbacks. For instance, modification-dependent interactions cannot be detected. Moreover, the method uses the pleiotropic Ras pathway and may cause technical complications.

SUMMARY OF THE INVENTION

Provided is a recombinant transmembrane receptor comprising an extracellular ligand-binding domain and a cytoplasmic domain that includes a heterologous bait polypeptide. The recombinant receptor is activated by binding a ligand to the ligand-binding domain and by binding a prey polypeptide to the heterologous bait polypeptide. As used herein, the term "receptor" may be used interchangeably with the term "recombinant receptor." The recombinant receptor may be a chimeric receptor in which the ligand-binding domain and the cytoplasmic domain are derived from two different receptors. The recombinant receptor may also be a multimerizing receptor, such as a homomultimerizing receptor or a heteromultimerizing receptor.

The cytoplasmic domain of the recombinant receptor comprises a heterologous bait polypeptide which may be fused to a carboxy terminal end, may replace a part of the carboxy terminal end, or may be situated in the cytoplasmic domain as an insertion or a replacement of an endogenous internal fragment. If the recombinant receptor is a heteromultimerizing receptor, then all chains may not comprise the bait since it is sufficient that one of the chains comprises the bait in the cytoplasmic domain of the receptor. When at least one of the activation sites in the cytoplasmic domain of the receptor is inactivated, the recombinant receptor is not activated. Thus, there is no active signaling pathway if only a ligand binds to the ligand-binding domain of the recombinant receptor.

The recombinant receptor may be inactivated in several ways. In one way, the amino acid required for activation is replaced by another amino acid. Other ways include changing the amino acid context of the activation site or deleting the activation site. For instance, insertion of the heterologous bait polypeptide and inactivation of the activation sites may result in one or more deletions of the original cytoplasmic domain. However, the cytoplasmic domain is that the cytoplasmic domain should retain, directly or indirectly, its inherent modifying enzyme activity by retaining a modifying enzyme activity binding site, such as a Jak binding site, or by incorporating an active modifying enzyme activity in the cytoplasmic domain. By maintaining the modifying enzyme activity, activation of the receptor and the signaling pathway is still achieved since a ligand will bind to the ligand-binding domain and a prey polypeptide will bind to the heterologous bait polypeptide in the cytoplasmic domain of the receptor.

The gene encoding the recombinant receptor which includes the bait polypeptide may be placed downstream from a constitutive or inducible promoter. The inducible promoter may have some advantages in cases where a competition exists for the binding site between prey polypeptides and endogenous polypeptides. Inducing the recombinant receptor in the presence of prey polypeptides may facilitate binding and avoid saturating the binding sites with endogenous polypeptides.

In one embodiment of the invention, a recombinant receptor includes a phosphorylation site as the activation site and the modifying enzyme activity is a kinase.

In another embodiment of the invention, a homomultimerizing recombinant leptin receptor has a heterologous bait polypeptide fused into or at the carboxy terminal end of its cytoplasmic domain. In this embodiment, the heterologous bait polypeptide may replace part of the cytoplasmic domain. Alternatively, three conserved tyrosine phosphorylation sites of the cytoplasmic domain may be inactivated by replacing the tyrosine residues with phenylalanine residues.

In another embodiment, a homomultimerizing recombinant receptor is disclosed in which an inactivated cytoplasmic domain of the leptin receptor, including a heterologous bait polypeptide as described herein, is fused to the ligand-binding domain of the erythropoietin (EPO) receptor.

In yet another embodiment, a heteromultimerizing recombinant receptor with the inactivated cytoplasmic domain of the leptin receptor, including a heterologous bait polypeptide, is fused to the interleukin-5 receptor α-chain ligand-binding domain of one subunit, wherein the other subunit is fused to the interleukin-5 receptor β-chain.

In a further embodiment, a heteromultimerizing recombinant receptor is disclosed wherein the inactivated cytoplasmic domain of the leptin receptor, including a heterologous bait polypeptide, is fused to the GM-CSFα-chain ligand-binding domain of one subunit, wherein the other subunit is fused to the interleukin-5 receptor β-chain.

In another aspect of the invention, a recombinant receptor comprising a ligand-binding domain and a cytoplasmic domain that includes a modified heterologous bait polypeptide is disclosed. The modification of the heterologous bait polypeptide may include, but is not limited to, phosphorylation, acetylation, acylation, methylation, ubiquitinilation, glycosylation or proteolytic processing. In this aspect, the recombinant receptor is activated by binding a ligand to the ligand-binding domain and by binding a prey polypeptide to the heterologous bait polypeptide, wherein the binding of the prey polypeptide to the heterologous bait polypeptide depends on the modification state of the heterologous bait polypeptide, i.e., the prey polypeptide binds if there is modification or no modification of the heterologous bait polypeptide. The modification state may be, but is not limited to, the presence or absence of phosphorylation, acetylation, acylation, methylation, ubiquitinilation, glycosylation, or proteolytic cleavage. The heterologous bait polypeptide may be modified by the bait-modifying enzyme activity which can be the modifying enzyme activity that modifies the activation site, although other bait-modifying enzyme activities may exist.

The recombinant receptor may be a chimeric receptor in which the ligand-binding domain and the cytoplasmic domain are derived from two different receptors. In one embodiment, the receptor is a multimerizing receptor. As described herein, the cytoplasmic domain of the recombinant receptor comprises a heterologous bait polypeptide which may be fused to the carboxy terminal end, may replace a part of the carboxy terminal end, or may be situated in the cytoplasmic domain as an insertion or a replacement of an endogenous internal fragment.

If the recombinant receptor is a heteromultimerizing receptor, then not all of the chains need to comprise the bait, since it is sufficient if one of the chains comprising the bait is in the cytoplasmic domain. When at least one of the activation sites in the cytoplasmic domain of the receptor has been inactivated, the receptor will not be activated and no active signaling pathway will exist if only a ligand binds the ligand-binding domain of the recombinant receptor. The inactivation of the cytoplasmic domain may be obtained in several ways, such as by replacing the amino acid required for activation with another amino acid, by changing the amino acid context of the activation site or by deleting the activation site. Insertion of the heterologous bait polypeptide and inactivation of the activation sites may result in one or more deletions of the original cytoplasmic domain. Regardless of the inactivation technique employed, the cytoplasmic domain should retain, directly or indirectly, its inherent modifying enzyme activity by retaining a modifying enzyme binding site or by incorporating an active modifying enzyme activity in the cytoplasmic domain.

The modification of the bait may be in cis or in trans, i.e., the enzymatic activity may be situated on the same cytoplasmic domain or the enzymatic activity may come from elsewhere. As described herein, the modification of the bait may be induced by binding a ligand to the ligand-binding domain. In one embodiment, a homodimerizing receptor where the bait is phosphorylated by an inherent kinase activity of the cytoplasmic domain, such as a Jak kinase that binds to the cytoplasmic domain, is disclosed. In another embodiment, a heteromultimerizing receptor where the cytoplasmic domain of one chain includes a bait to be modified and the cytoplasmic domain of another chain includes the bait-modifying enzyme activity is disclosed.

As described herein, the receptor and the signaling pathway may be activated by binding a ligand to the ligand-binding domain and by binding a prey polypeptide to the heterologous bait polypeptide situated in the cytoplasmic domain of the receptor. Binding of the prey polypeptide may depend on the modification state of the heterologous bait polypeptide, i.e., binding occurs when the bait is modified or when the bait is not modified.

In another aspect of the invention, a prey polypeptide comprising a fusion protein of two polypeptides is disclosed. The first polypeptide interacts, directly or indirectly, with a bait polypeptide and the second polypeptide includes at least one activation site. The activation site may be a phosphorylation site, such as a tyrosine phosphorylation site. The tyrosine phosphorylation site may be part of a Signal Transducer and Activator of Transcription (STAT) binding site such as a STAT1 and/or STAT3 binding site. As used herein, the phrase "direct interaction" will refer to a direct protein-protein contact between the heterologous bait polypeptide and the prey polypeptide. The phrase "indirect interaction" as used herein will refer to the heterologous bait polypeptide interacting with one or more other polypeptides, and subsequently forming a complex that interacts with the prey polypeptide or vice versa. In the indirect interaction, the prey polypeptide may interact with one polypeptide or with several polypeptides from the complex. The binding of the prey polypeptide to the bait polypeptide may also be dependent on the modification state of the bait polypeptide and/or of proteins within the binding complex.

When interactions of nuclear proteins are studied using the teachings of the invention, the prey polypeptide may comprise a Nuclear Export Sequence (NES) to ensure that it is available in the cytosol. The NES signal (amino acids 37-46) of the heat-stable inhibitor of the cAMP-dependent protein kinase has been shown to override a strong nuclear localization signal (Wiley et al., 1999). Thus, the NES signal helps keep the prey polypeptide in the cytoplasm even when a strong nuclear localization signal is present, thus facilitating interaction with the bait.

In one embodiment, a prey polypeptide of the invention is disclosed wherein the prey polypeptide interacts with the heterologous bait polypeptide of a recombinant receptor. Upon binding of a ligand to the ligand-binding domain of the recombinant receptor and upon interaction, directly or indirectly, of the heterologous bait polypeptide with the prey polypeptide, the activation site of the prey polypeptide may be modified by the modifying enzyme activity of the cytoplasmic domain of the receptor. Modification of the activation site will activate the signaling pathway. In the illustrated embodiment, the activation site is a phosphorylation site and the modifying enzyme activity is a kinase activity. In an illustrative embodiment, the activation may comprise binding of a STAT polypeptide to the phosphorylated phosphorylation site, followed by phosphorylation of the STAT polypeptide and subsequent dimerization of two phosphorylated STAT molecules.

In another aspect of the invention, a vector encoding a recombinant receptor of the invention and/or a vector encoding a prey polypeptide of the invention is disclosed. The recombinant receptor and the prey polypeptide may be situated on the same or separate vectors. The vector may be any vector known by a person skilled in the art, including, but not limited to, episomal vectors, integrative vectors and viral vectors. In one embodiment, a bait vector where the bait is integrated in the chromosome by a recombinase-assisted integration, such as cre-lox or flp-frt, and/or a retroviral prey vector that allows for retroviral integration in the genome are disclosed.

In another aspect, a eukaryotic cell comprising a recombinant receptor of the invention is disclosed. In one embodiment, the eukaryotic cell is transformed or transfected with one or more vectors of the invention. The eukaryotic cell may comprise, but is not limited to, a yeast cell, a fungal cell, a plant cell, an insect cell or other mammalian cells. In one embodiment, the eukaryotic cell is a mammalian cell. In another embodiment, a eukaryotic cell line expressing the mouse retroviral receptor is disclosed, thus allowing safe retroviral work using retroviral cDNA libraries.

In another aspect, a kit comprising one or more cloning vectors which allow for the construction of one or more vectors of the invention is disclosed. It will be apparent by those skilled in the art that a cloning vector encoding a recombinant receptor with the cytoplasmic domain may include one or more restriction sites which allow for an "in-frame" fusion of a nucleic acid fragment encoding a polypeptide. Thus, the cloning vector may be used to construct a vector encoding a recombinant receptor of the invention. In a similar manner, a cloning vector encoding a first polypeptide with at least one activation site may include one or more restriction sites, such that an "in-frame" fusion of a nucleic acid fragment encoding a second polypeptide may be fused to the first polypeptide. In this manner, a vector encoding a prey polypeptide of the invention may be constructed. Alternatively, other cloning strategies known by those skilled in the art may be used to construct vectors encoding the recombinant receptor and vectors encoding the prey polypeptide.

In yet another aspect, a method to detect compound-compound binding using a recombinant receptor and/or a prey polypeptide is disclosed. In one embodiment, a eukaryotic cell carrying a recombinant receptor of the invention is transformed or transfected with a vector library encoding prey polypeptides. Bait-prey binding will result in an activation of the signaling pathway which can be detected with a reporter system.

A chimeric receptor may also be used in the disclosed method. By using the chimeric receptor in the disclosed method, a nonbait-specific background may be eliminated. By using two different receptors, such as a nonbait-comprising receptor and a bait-comprising receptor, a difference between bait-specific and nonbait-specific binding may be realized by using a host cell carrying at least two receptors.

A first receptor of the host cell may include a first ligand-binding domain and a cytoplasmic domain without an activation site or a heterologous bait polypeptide. A second receptor of the host cell may include the inactivated cytoplasmic domain, a heterologous bait polypeptide and a second ligand-binding domain. Upon exogenous addition of the first ligand to the medium and binding of the first ligand to the receptor, a positive signal may be detected in the cells when a nonbait-specific interaction occurs between a prey polypeptide and the cytoplasmic domain of the receptor, wherein the prey polypeptide is fused to a polypeptide comprising an activation site. The cells may then be selected and/or eliminated. After selection and/or elimination of the nonbait-specific interacting preys, the second ligand may be added to the medium. Upon binding of the second ligand to the ligand-binding domain, a positive signal may be detected upon specific bait-prey interaction as the prey polypeptides binding to the cytoplasmic domain have been removed. The chimeric receptor allows a subtractive selection to be made for preys binding to closely related, but different baits.

An illustrative embodiment of the method to detect compound-compound binding is a method wherein the binding is a protein-protein interaction. Another illustrative embodiment is a method to detect protein-protein interaction wherein the interaction is modification state dependent. Yet another illustrative embodiment is a method to detect compound-compound binding wherein the binding is mediated by three or more partners. In this embodiment, one or more of the partners may not be or not completely be of proteinaceous nature. It will be apparent by a person skilled in the art that a recombinant receptor of the invention may bind a small molecule. Alternatively, the prey polypeptide of the invention may also bind to the small molecule, such that bait and prey are linked together by the small molecule. The small molecule may be present in the host cell as a compound produced by the cell or as a compound taken up by the cell from the medium.

The method to detect compound-compound binding includes the construction of a eukaryotic cell comprising a recombinant receptor of the invention, followed by transformation or transfection of the cell with a library of prey polypeptide vectors of the invention. The compound-compound binding may be detected by activating the receptor, thus leading to an active signaling pathway and resulting in the induction of a reporter system. The reporter system may be any system that allows for the detection and/or the selection of the cells which carry a recombinant receptor of the invention. Several different reporter systems may be used including, without limitation, a luciferase gene, an antibiotic resistance gene or a cell surface marker gene placed after a promoter and induced by the signaling pathway. Alternatively, reporter systems based on the change in characteristics of compounds of the signaling pathway may be used, wherein the signaling pathway is active upon the phosphorylation and/or dimerization of the compounds.

Thus, provided is a protein-protein interaction selection system that studies the protein-protein interactions under physiological conditions, with a low and controllable background, and by which modification-dependent protein-protein interactions can be isolated.

"NC" refers to a non-stimulated negative control. Stimulations were carried out as described in the examples.

Figure 3:
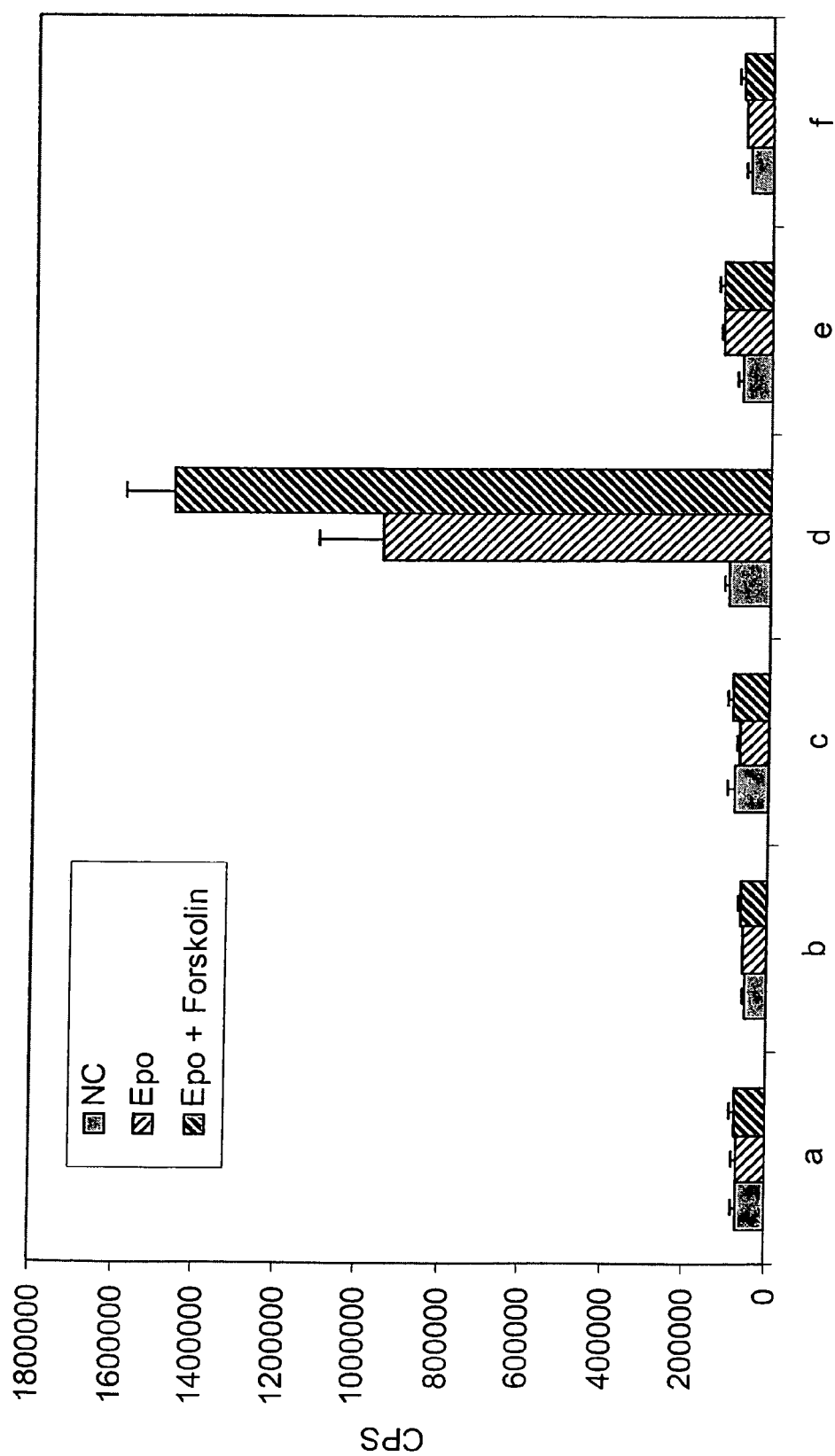

FIG. 3: Functionality of p53-SV40 LargeT interaction trap measured by luciferase light emission in a chemiluminescence counter (cps). The cells were transfected with:
   (a)       pSV-SPORT+pMG1-SVT+pGL3-rPAP1-luci+pUT651;
   (b)        pSV-SPORT+pMG1-CIS+pGL3-rPAP1-luci+pUT651;
   (c)      pSV-SPORT+pMET7-SVT+pGL3-rPAP1-luci+pUT651;
   (d)        pSEL1-p53+pMG1-SVT+pGL3-rPAP1-luci+pUT651;
   (e) pSEL1-p53+pMG1-CIS+pGL3-rPAP1-luci+pUT651; and
   (f)        pSEL1-p53+pMET7-SVT+pGL3-rPAP1-luci+pUT651.

"NC" refers to a non-stimulated negative control. Stimulations were carried out as described in the examples.

Figure 4:
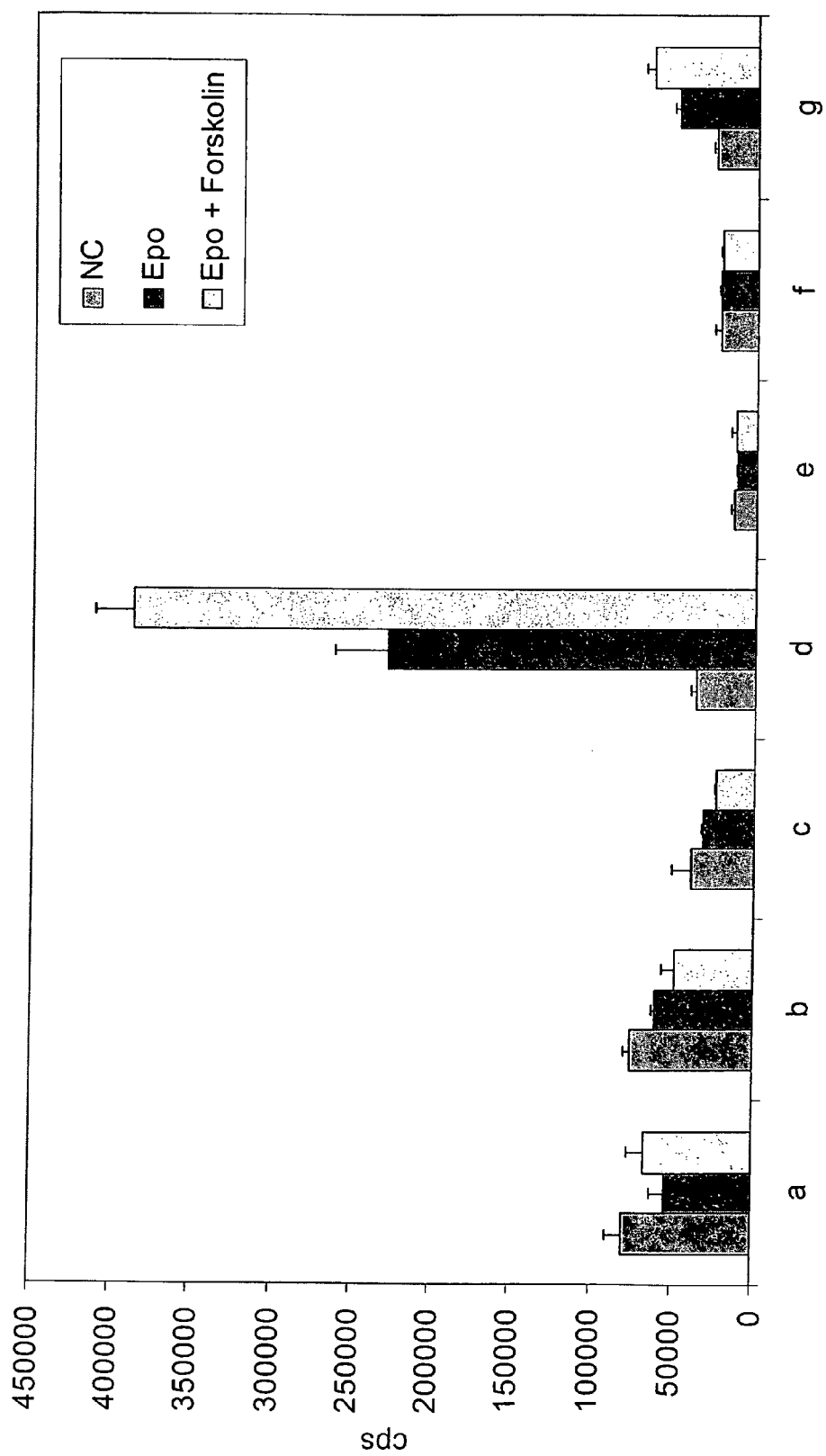

FIG. 4: Functionality of the EpoR-CIS phosphorylation-dependent interaction trap measured by luciferase light emission in a chemiluminescence counter (cps). The cells were transfected with:
   (a)          pSV-SPORT+pMG1-CIS+pGL3-rPAP1-luci+pUT651;
   (b)         pSV-SPORT+pMG1-SVT+pGL3-rPAP1-luci+pUT651;
   (c) pSV-SPORT+pEF-FLAG-I/mCIS+pGL3-rPAP1-luci+pUT651;
   (d)         pSEL1-EpoR+pMG1-CIS+pGL3-rPAP1-luci+pUT651;
   (e)    pSEL1-EpoR+pEF-FLAG-I/mCIS+pGL3-rPAP1-luci+pUT651;
   (f)     pSEL1-EpoRY-F+pMG1-CIS+pGL3-rPAP1-luci+pUT651; and
   (g)        pSEL1-EpoR+pMG1-SVT+pGL3-rPAP1-luci+pUT651.

"NC" refers to the non-stimulated negative control. Stimulations were carried out as described in the examples.

Figure 5:
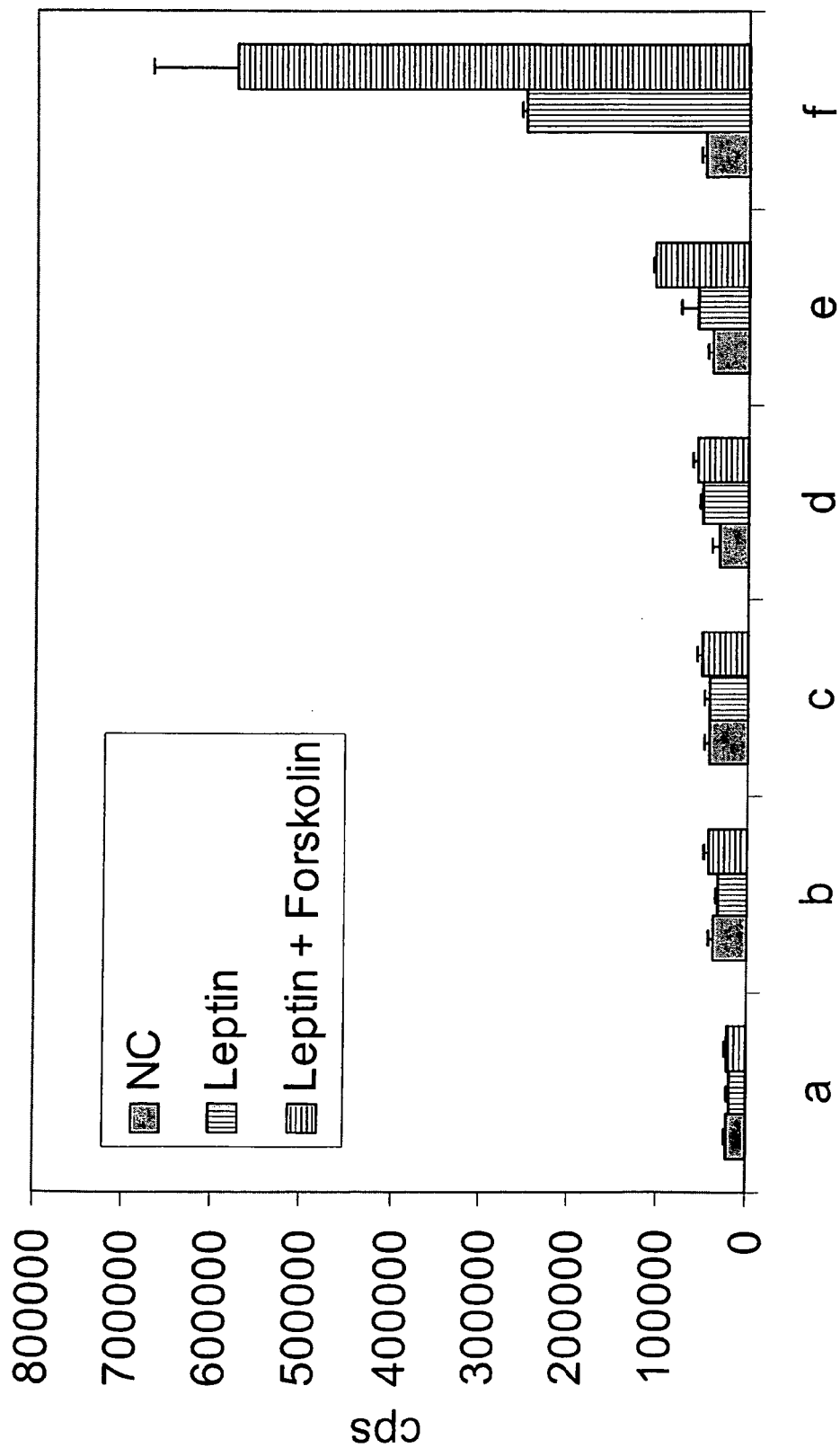

FIG. 5: Functionality of the IRS1-GRB2-Vav indirect interaction trap measured by luciferase light emission in a chemiluminescence counter (cps). The cells were transfected with:
   (a) pMET7mcs+pMG1-CIS+pGL3-rPAP1-luci+pUT651;
   (b)       pMET7mcs+pMG1-GRB2S+pGL3-rPAP1-luci+pUT651;
   (c)          pMET7mcs+pMG1-VavS+pGL3-rPAP1-luci+pUT651;
   (d) pMET7 LepR-IRS1+pMG1-CIS+pGL3-rPAP1-luci+pUT651;
   (e) pMET7 LepR-IRS1+pMG1-GRB2S+pGL3-rPAP1-luci+pUT651; and
   (f) pMET7 LepR-IRS1+pMG1-VavS+pGL3-rPAP1-luci+pUT651.

"NC" refers to the non-stimulated negative control. Stimulations were carried out as described in the examples.

Figure 6:
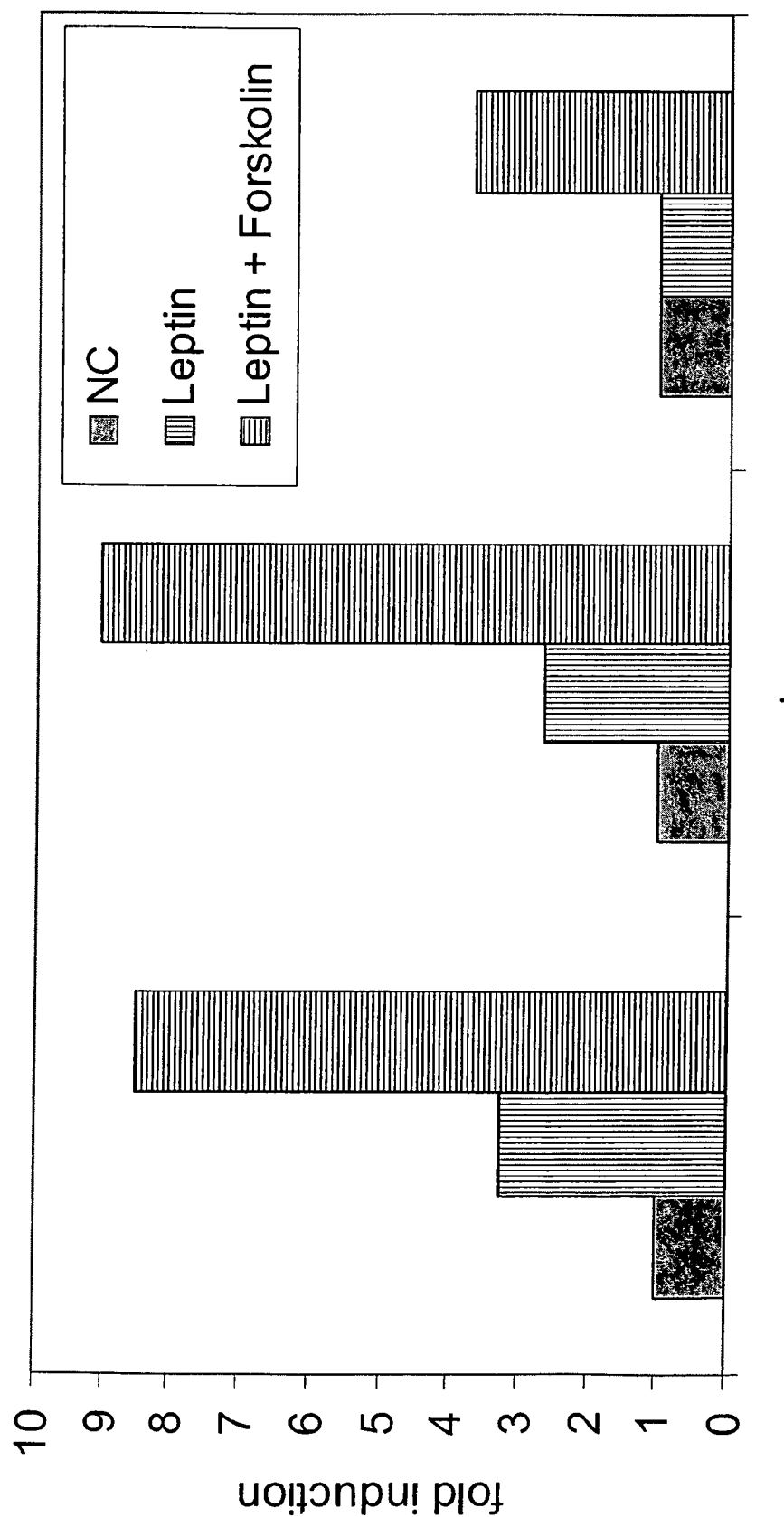

FIG. 6: Functionality of the IRS1-GRB2-Vav indirect interaction trap measured by luciferase light emission in a chemiluminescence counter (cps): GRB2 dose dependent inhibition of the signal. The cells were transfected with:
   (a) pMET7 LepR-IRS1+200 ng pMG1-VavS+pGL3-rPAP1-luci+pUT651;
   (b) pMET7 LepR-IRS1+200 ng pMG1-VavS+200 ng pMET7 GRB2SH3+pGL3-rPAP1-luci+pUT651; and
   (c) pMET7 LepR-IRS1+200 ng pMG1-VavS+1000 ng pMET7 GRB2SH3+pGL3-rPAP1-luci+pUT651.

"NC" refers to the non-stimulated negative control. Stimulations were carried out as described in the examples.

Figure 7:
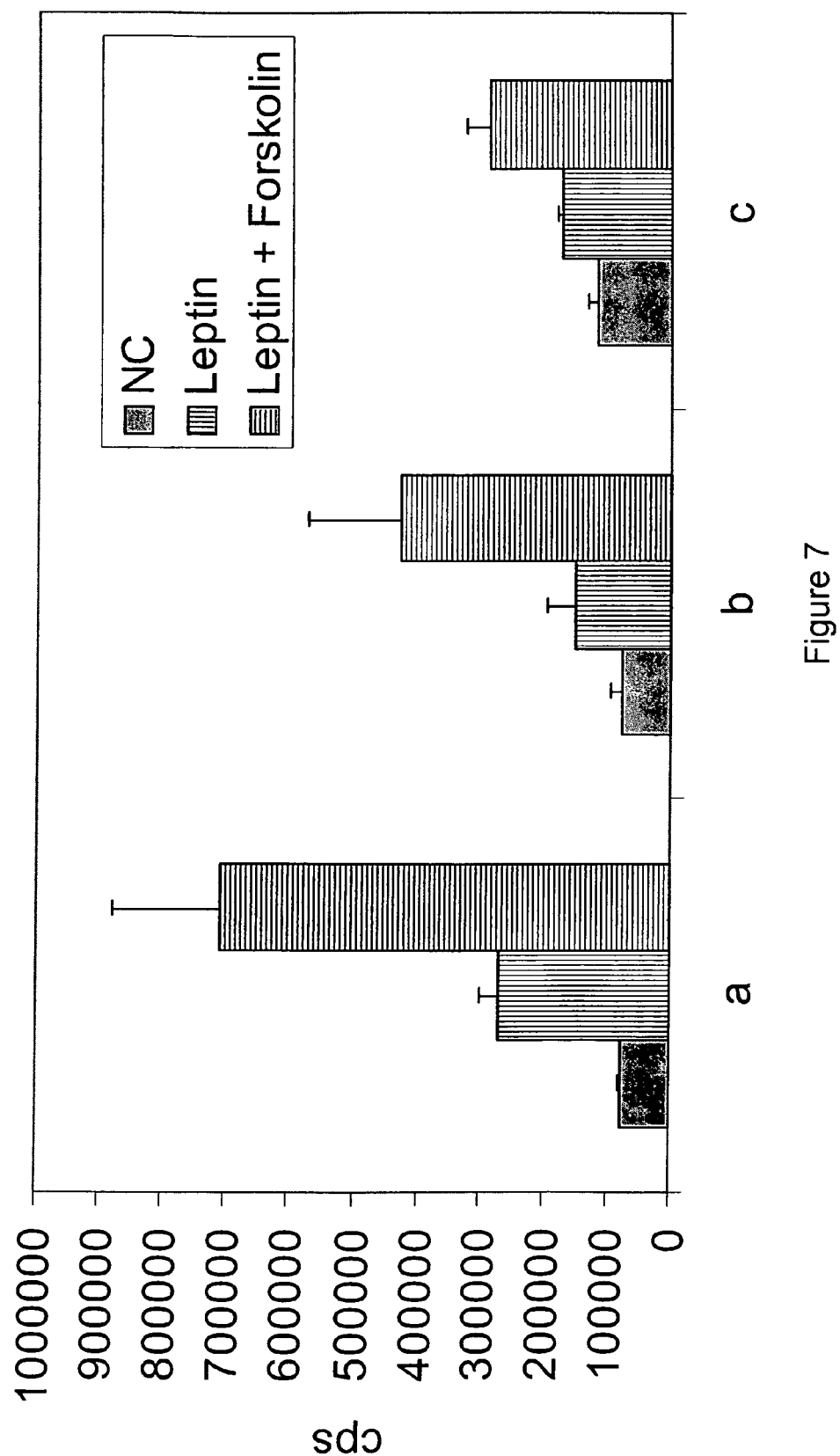

FIG. 7: Functionality of the IRS1-GRB2-Vav indirect interaction trap measured by luciferase light emission in a chemiluminescence counter (cps): VavS dose dependent inhibition of the signal. The cells were transfected with:
   (a) pMET7 LepR-IRS1+200 ng pMG1-VavS+pGL3-rPAP1-luci+pUT651;
   (b) pMET7 LepR-IRS1+200 ng pMG1-VavS+200 ng pMET7 VavS+pGL3-rPAP1-luci+pUT651; and
   (c) pMET7 LepR-IRS1+200 ng pMG1-VavS+1000 ng pMET7 VavS+pGL3-rPAP1-luci+pUT651.

"NC" refers to the non-stimulated negative control. Stimulations were carried out as described in the examples.

Figure 8:
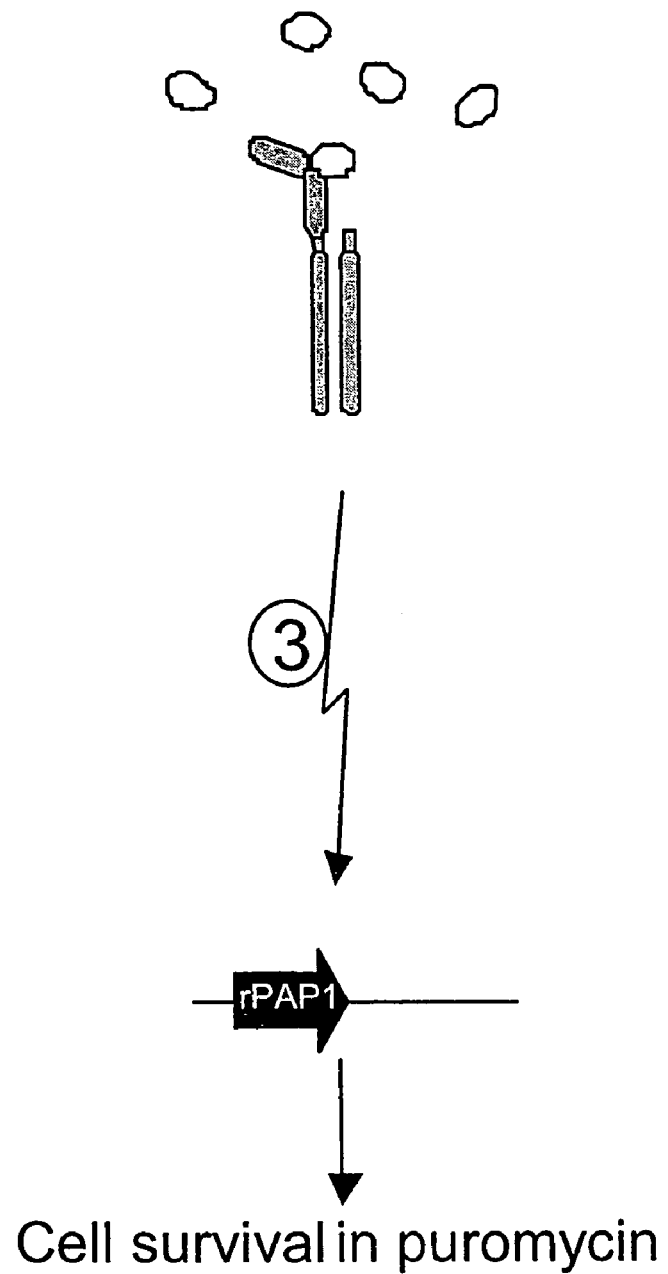

FIG. 8: Layout of an optimized MAPPIT-based two-hybrid screening method. The illustrated procedure encompasses three successive steps indicated with encircled numbers. First, cells expressing the chimeric receptor with the C-terminal "bait" (CR-Bait) are generated by recombinase-assisted genomic integration and followed by hygromycin selection. Next, gp130-"prey" chimeras are expressed by retroviral gene transfer. Finally, if cognate "bait"-"prey" interaction occurs, ligand binding induces a signaling cascade and leads to induction of the puromycin resistance marker and, thus, concomitant formation of cell colonies in selective medium. Direct RT-PCR amplification of "prey" encoding transcripts from lysed cell colonies allows for rapid "prey" identification.

FIGS. 9A-G: generally illustrate the MAPPIT procedure for two-hybrid screening.

Figures 9A, 9B:
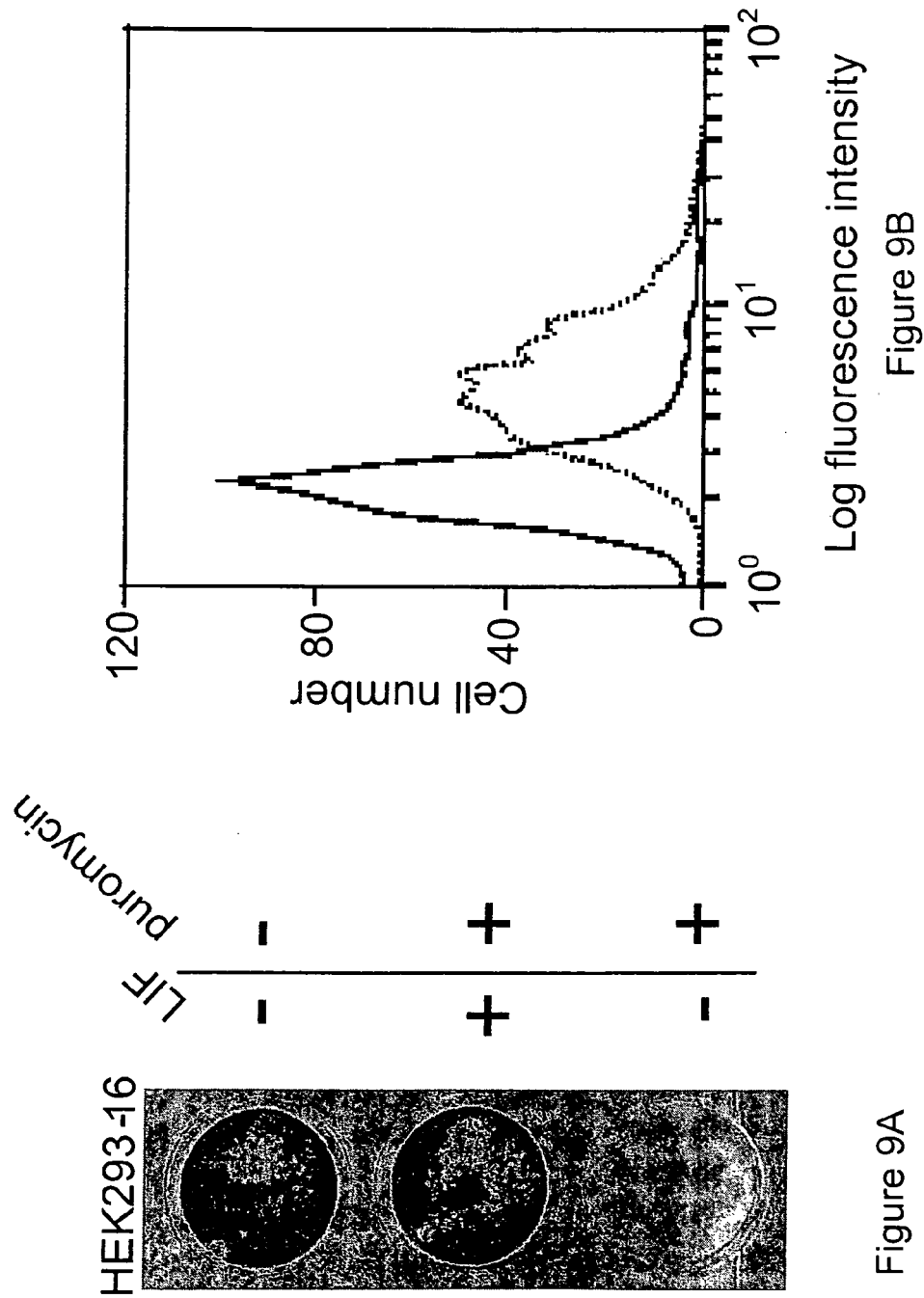

FIG. 9A: The HEK293-16 cell line shows ligand-induced puromycin resistance. HEK293-16 cells were seeded in a 24-well plate and left untreated (top well) or subjected to puromycin selection (1 µg/ml) with (middle well) or without (bottom well) prior to activation of gp130 using LIF for 48 hours. After one week, surviving cells were stained with crystal violet.

FIG. 9B: Selection of isogenic HEK293-16 cells expressing the EpoR "bait." HEK293-16 cells were co-transfected with the pcDNA5/FRT-EpoR "bait," the Flp recombinase expression vectors, and selected for hygromycin resistance (100 µg/ml) for ten days. Cells were stained with polyclonal antiserum which recognizes the extracellular domain of the EpoR and Alexa488-labelled secondary antibody. Solid and dotted lines show parental or hygromycin-selected HEK293-16 cells, respectively.

FIG. 9C: Selection of cells based on a cognate "prey"-"bait" interaction. Hygromycin-resistant cells from FIG. 9B were seeded in a 24-well plate, infected with CIS "prey" expressing retrovirus (1/30 dilution of retroviral stock) for 48 hours, and were left untreated (top well) or stimulated with Epo for another 48 hours (middle well) prior to treatment with puromycin (1 µg/ml). The bottom well shows Epo-stimulated cells selected as above but which express irrelevant lacZ protein (1/3 dilution of retroviral stock). Surviving cells were stained with crystal violet after seven days.

FIG. 9D: Puromycin-resistant cells express the "prey" chimera. Parental HEK293-16 cells or puromycin-resistant cells from FIG. 9C were permeabilized, sequentially treated with anti-FLAG antibody and FITC-labeled secondary antibody, and subjected to FACS analysis. Solid and dotted lines show parental or puromycin-selected HEK293-16 cells, respectively. (INSET) RT-PCR detection of transcripts encoding the "prey" chimera. Cells from FIG. 9C were lysed and the "prey"-encoding transcript was amplified by RT-PCR. The arrow indicates the CIS-specific amplicon which was verified by DNA sequencing. A negative control was also performed on parental cells (middle lane). "M" represents a marker lane.

Figure 9E:
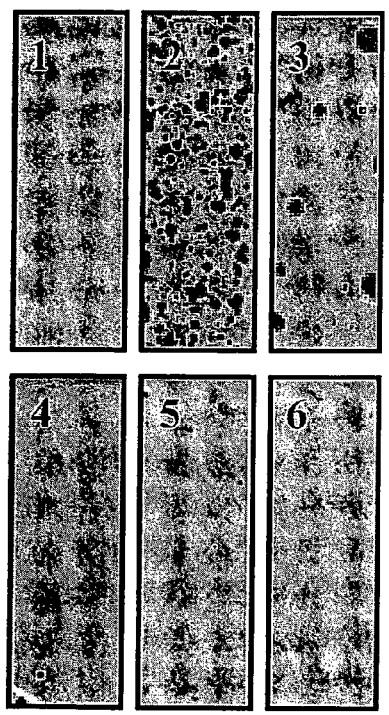

FIG. 9E: Dose-dependent recovery of gp130-CIS "prey" expressing cell clones. EpoR "bait" expressing cells were seeded in 75 cm$^2$ culture flasks and infected with CIS "prey" expressing retrovirus 1/10 serially diluted in a complex retroviral HEK293 cDNA library. After selection, puromycin-resistant colonies were stained with crystal violet. Panel 1 shows cells infected with a 1/10 dilution of CIS "prey," but without Epo stimulation. Panels 2-5 show the 1/10 to 1/10,000 serial dilutions and panel 6 shows the outcome of cells infected with the retroviral cDNA library in the absence of CIS "prey." In a parallel "spiking" experiment, 19 out of 21 analyzed clones contained gp130-CIS "prey" transcripts.

Figure 9F:
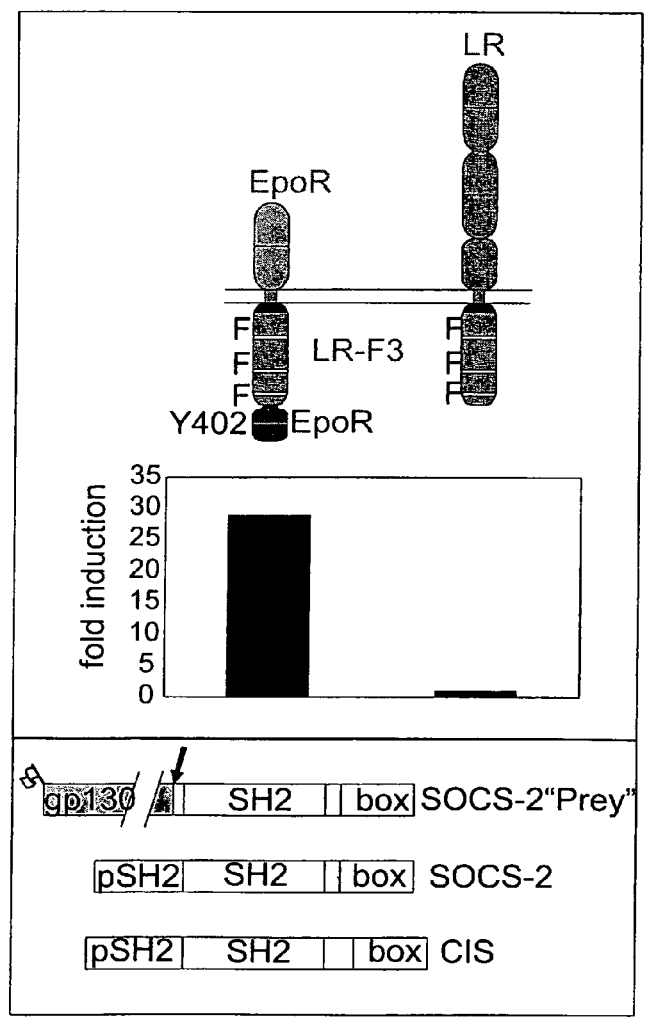

FIG. 9F: Functional analysis of the EpoR "bait"-SOCS-2 "prey" interaction. MAPPIT screening of an HEK293 cDNA library using the EpoR "bait" resulted in the isolation of a cell clone expressing a SOCS-2 "prey" construct. This selected clone was transiently transfected with the pXP2d2-rPAP1-luci reporter alone or in combination with the vector encoding the LR-F3 variant, was stimulated with Epo or leptin for 24 hours, respectively, or left unstimulated. The upper panel shows the corresponding luciferase inductions with a diagrammatic presentation of the activated receptors on top. In the lower panel, a graphic representation of the SOCS-2 "prey" chimera and of intact SOCS-2 and CIS is shown.

Figure 9G:
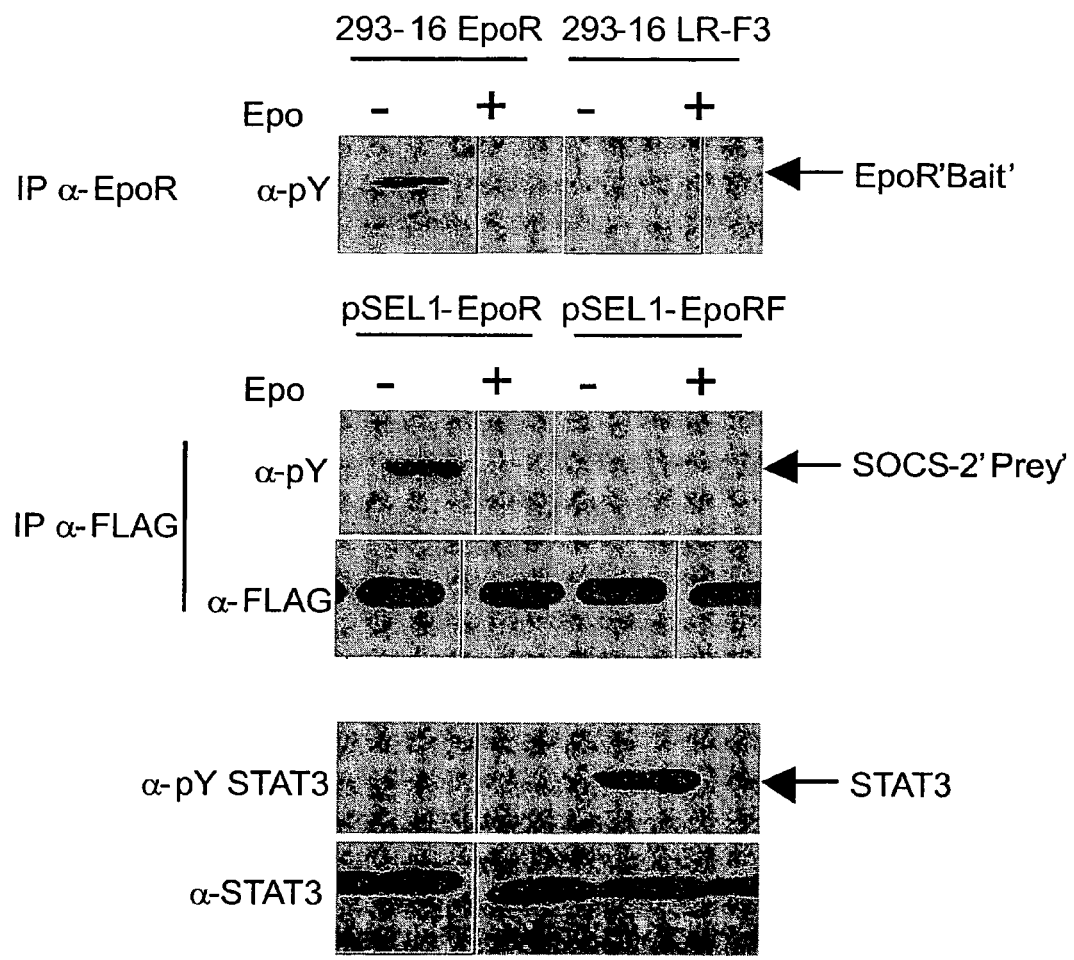

FIG. 9G: The EpoR "bait"-SOCS-2 "prey" interaction is phosphorylation dependent. (Upper panel) HEK293-16 cells expressing chimeric receptors with (293-16 EpoR) or without (293-16 LR-F3) the EpoR "bait" were stimulated with Epo or left untreated. Ligand-dependent phosphorylation of the EpoR "bait" is observed in contrast to lack of phosphorylation of the LR-F3 chimera. (Middle and lower panels) HEK293T cells were transiently transfected with expression constructs for the EpoR "bait" (pSEL1-EpoR) and the SOCS-2 "prey." The middle panel and lower panel, respectively, show ligand-dependent "prey" and STAT3 phosphorylation, which is only observed upon transfection with pSEL1-EpoR, but not with pSEL1-EpoRF. Expression controls for the SOCS-2 "prey" and for STAT3 are also shown.

Figure 10:
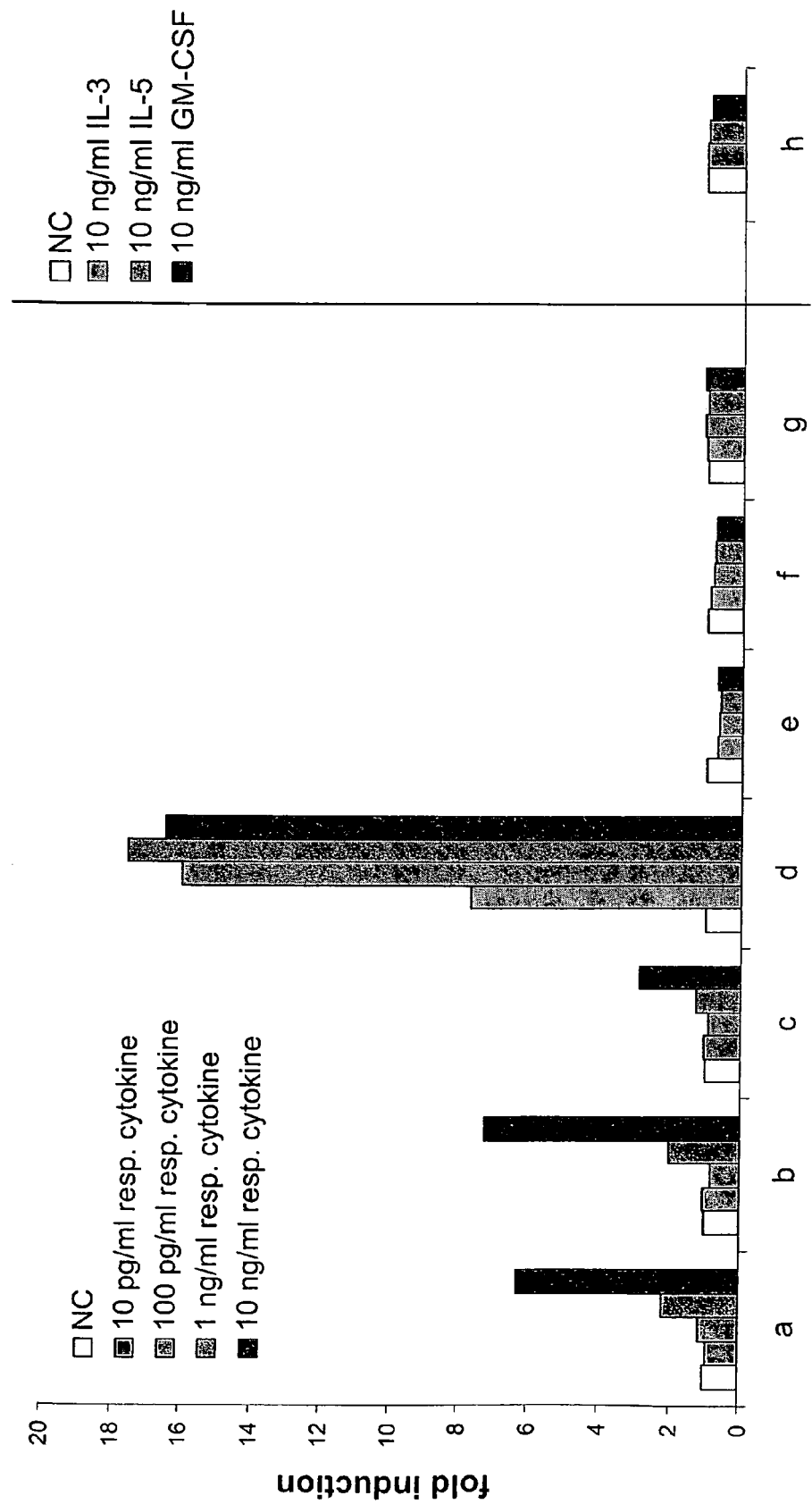

FIG. 10: Functionality of IL3R-, IL5R- and GM-CSFR-LepR chimera in the Hek 293T cell line measured by luciferase light emission in a chemiluminescence counter (cps). The cells were transfected with:

(a) pSV-SPORT-EpoR/LepR+pGL3-rPAP1-luci+pUT651;
(b) pSV-SPORT-IL-3Rα/LepR+pSV-SPORT-β$_c$/LepR+pGL3-rPAP1-luci+pUT651;
(c) pSV-SPORT-IL-5Rα/LepR+pSV-SPORT-β$_c$/LepR+pGL3-rPAP1-luci+pUT651;
(d) pSV-SPORT-GM-CSFRα/LepR+pSV-SPORT-βc/LepR+pGL3-rPAP1-luci+pUT651;
(e) pSV-SPORT-IL-3Rα/LepR+pGL3-rPAP1-luci+pUT651;
(f) pSV-SPORT-IL-5Rα/LepR+pGL3-rPAP1-luci+pUT651;
(g) pSV-SPORT-GM-CSFRα/LepR+pGL3-rPAP1-luci+pUT651; and
(h) pSV-SPORT-β$_c$/LepR+pGL3-rPAP1-luci+pUT651.

"NC" represents the non-stimulated negative control. Stimulation was as described in the examples.

Figure 11:
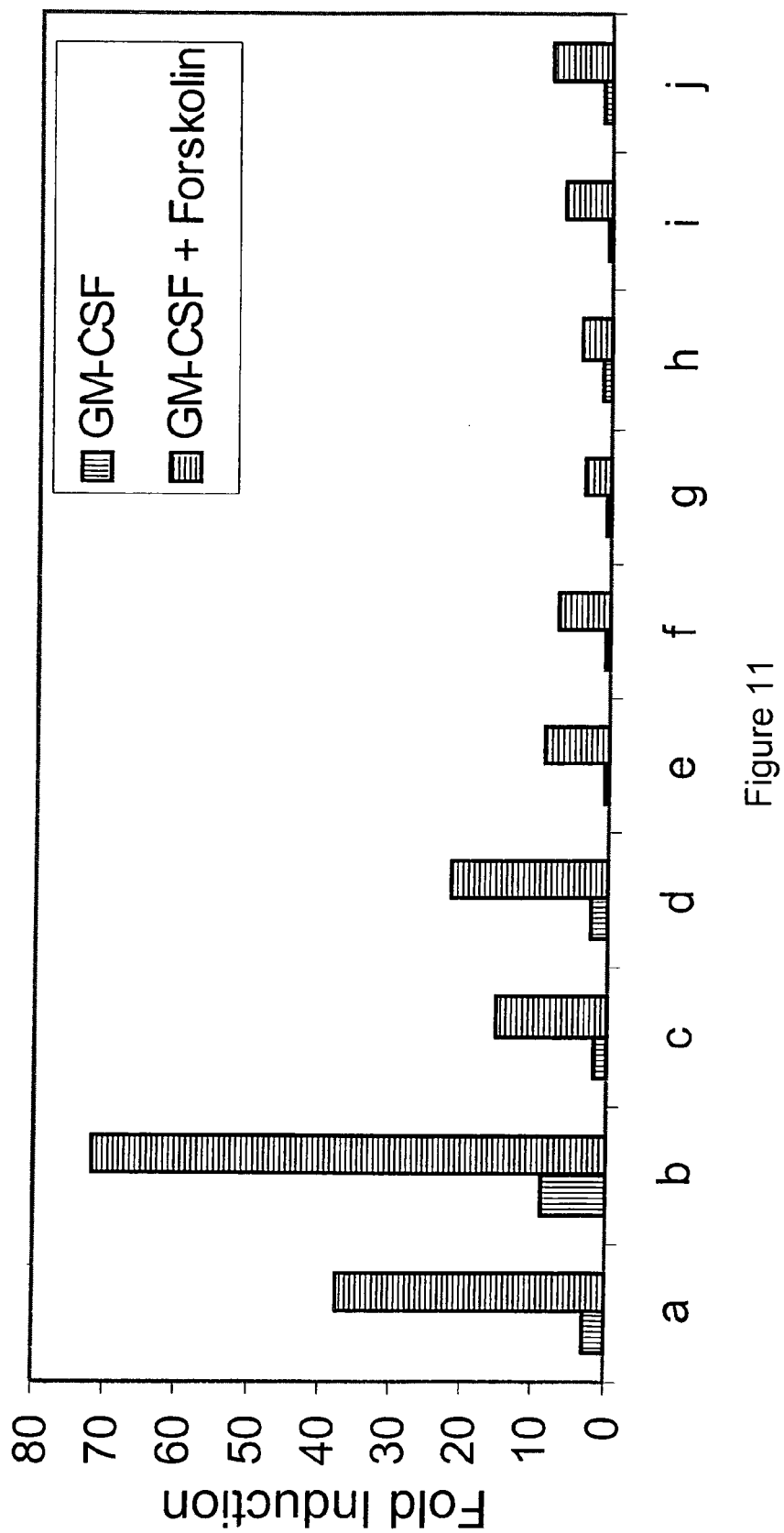

FIG. 11: Functionality of the Smad3-Smad4 phosphorylation-dependent interaction trap measured by luciferase light emission in a chemiluminescence counter (cps). The cells were transfected with:

(a) pSV-SPORT-β$_c$/LepR-F3-ALK4CA+pSV-SPORT-GM-CSFRα/LepR-F3-Smad3+pMG2-Smad4+pXP2d2-rPAP1luci+pUT651;
(b) pSV-SPORT-β$_c$/LepR-F3-Smad3+pSV-SPORT-GM-CSFRα/LepR-F3-ALK4CA+pMG2-Smad4+pXP2d2-rPAP1 luci+pUT651;
(c) pSV-SPORT-β$_c$/LepR-F3+pSV-SPORT-GM-CSFRα/LepR-F3-Smad3+pMG2-Smad4+pXP2d2-rPAP1luci+pUT651;
(d) pSV-SPORT-β$_c$/LepR-F3-Smad3+pSV-SPORT-GM-CSFRα/LepR-F3+pMG2-Smad4+pXP2d2-rPAP1luci+pUT651;
(e) pSV-SPORT-β$_c$/LepR-F3-ALK4CA+pSV-SPORT-GM-CSFRα/LepR-F3+pMG2-Smad4+pXP2d2-rPAP1luci+pUT651;
(f) pSV-SPORT-β$_c$/LepR-F3+pSV-SPORT-GM-CSFRα/LepR-F3-ALK4CA+pMG2-Smad4+pXP2d2-rPAP1 luci+pUT651;
(g) pSV-SPORT-β$_c$/LepR-F3-ALK4CA+pSV-SPORT-GM-CSFRα/LepR-F3-Smad3+pMG2+pXP2d2-rPAP1 luci+pUT651;
(h) pSV-SPORT-β$_c$/LepR-F3-Smad3+pSV-SPORT-GM-CSFRα/LepR-F3-ALK4CA+pMG2+pXP2d2-rPAP1luci+pUT651;

(i) pSV-SPORT-β$_c$/LepR-F3-ALK4CA+pSV-SPORT-GM-CSFRα/LepR-F3-Smad3+pMET7-Smad4+pXP2d2-rPAP1 luci+pUT651; and (j) pSV-SPORT-β$_c$/LepR-F3-Smad3+pSV-SPORT-GM-CSFRα/LepR-F3-ALK4CA+pMET7-Smad4+pXP2d2-rPAP1luci+pUT651.

DETAILED DESCRIPTION OF THE INVENTION

The following definitions are set forth:

The term "receptor" as used herein does not necessarily indicate a single polypeptide, but may be used to refer to a receptor complex including two or more polypeptides, and may further include a ligand-binding domain and a cytoplasmic domain. The term "recombinant receptor" indicates that at least one of the polypeptides, such as the cytoplasmic domain, is recombinant.

The term "activation site" as used herein refers to the site of a receptor that, in the wild-type receptor, is modified after binding of a ligand to the ligand-binding domain, thus leading to a reorganization of the receptor and subsequent activation of the modifying enzyme activity. "Activation site" also refers to a site to which a compound of the signaling pathway can bind after modification or any site that performs a similar function. In the latter case, the activation site is not necessarily located on the same polypeptide as the wild-type receptor, but may be situated on another polypeptide of the receptor complex.

"Modifying enzyme activity" as used herein refers to the enzymatic activity associated with or incorporated in the cytoplasmic domain of the receptor that is normally induced upon binding of the ligand to the ligand-binding domain and subsequent reorganization of the receptor (e.g., by a conformational change) which may modify the activation site. The activation site may be a phosphorylation site and the modifying enzyme activity may be a kinase activity. The phrase "bait-modifying enzyme activity" refers to the activity that modifies the bait and may be substantially similar to the modifying enzyme activity.

The phrase "activation of a receptor" as used herein refers to the receptor inducing a signaling pathway, such as by binding a compound of the signaling pathway to the modified activation site, wherein the activation typically results in the induction or repression of one or more genes. The gene may be a reporter gene such that the activation of the receptor may be monitored.

An "activated receptor" refers to a receptor where the binding of a compound to the activation site has been enabled by modification of the site. A receptor in which the modifying enzyme activity has been induced without modification of an activation site is not considered as activated.

"Multimerizing receptor" as used herein indicates that the activated receptor comprises several polypeptides, but does not necessarily imply that the multimerization is induced by ligand binding because the receptor can exist as a preformed complex wherein the conformation is changed upon ligand binding.

The term "polypeptide" as used herein refers to any proteinaceous structure independent of length and includes molecules such as peptides, phosphorylated proteins and glycosylated proteins. "Polypeptide" does not necessarily indicate an independent compound, but may also refer to a part of a bigger compound, such as a domain of a protein.

The phrase "heterologous bait polypeptide" will be used herein to refer to a polypeptide comprised in the cytoplasmic domain of a receptor, and indicates that the polypeptide is within the cytoplasmic domain, or fused to the cytoplasmic domain; there is another polypeptide that is not present in the cytoplasmic domain of the non-recombinant receptor. The "heterologous bait polypeptide" may replace a part of the cytoplasmic domain. The term "bait" as used herein indicates that the polypeptide can interact with other polypeptides which do not belong to the normal receptor complex.

"Prey polypeptide" as used herein refers to a fusion protein comprising one polypeptide that may bind with the heterologous bait polypeptide and another polypeptide that comprises at least one activation site.

The term "ligand" as used herein refers to every compound that can bind to the extracellular domain of a receptor and that is able to initiate the signaling pathway by binding the extracellular domain. "Initiating" as used herein refers to starting the events that normally follow the binding of the ligand to the extracellular domain of the receptor, e.g., multimerization for a multimerizing receptor, but does not imply activation of the receptor and/or activation of the signaling pathway.

"Compound," as used herein, refers to any chemical or biological molecule, including simple, complex, organic or inorganic molecules, peptides, peptido-mimetics, proteins, antibodies, carbohydrates, nucleic acids or derivatives thereof.

The terms "bind" and "binding" refer to any interaction, direct or indirect. A direct interaction implies a contact between the binding partners. An indirect interaction indicates any interaction wherein the interaction partners interact in a complex of more than two compounds. The interaction may be completely indirect with the help of one or more bridging compounds or may be partly indirect, wherein a direct contact stabilized by the interaction of one or more compounds exists.

The phrase "functional fragment of the inactivated leptin receptor cytoplasmic domain" refers to a fragment of the leptin receptor cytoplasmic domain that allows binding of the Jak kinases.

As used herein, "inactivation of an activation site" will refer to any change, mutation or deletion that inhibits a modification at the position of the potentially modified residue in the polypeptide. In particular, "inactivation of a tyrosine phosphorylation site" indicates any change, mutation or deletion that inhibits a phosphorylation at the position of the potentially phosphorylated tyrosine residue in the polypeptide. In the illustrated embodiment, the inactivation is a mutation or a change of tyrosine to phenylalanine at this position.

"Cloning vector" as used herein refers to a vector that is generally considered as an intermediate step for the construction of another vector. The "cloning vector" is intended to insert one or more nucleic acid fragments in order to obtain one or more new vectors that will be used to transform or transfect the host cell of interest, or used as cloning vectors themselves.

EXAMPLES

Materials and Methods
Cell Lines, Transfection and Infection Procedures

Transfections were performed according to the calcium phosphate method (Graham and van der Eb, 1973).

Recombinant mouse leptin, recombinant human leukemia inhibitory factor (LIF) and recombinant human erythropoietin (Epo) were obtained from R&D Systems. Stimulation conditions were 100 ng/ml leptin, 1 ng/ml LIF and 50 ng/ml Epo.

For production of ecotropic retrovirus harboring the gp130-CIS or LacZ coding sequence, φNX-Eco cells were seeded at a density of 6×10$^6$ cells/Petri dish the day prior to transfection. Cells were transfected with 50 µg of the retroviral vector pBG1-CIS according to the calcium phosphate procedure. Twenty-five µM chloroquine was added 5 minutes before transfection. Medium was harvested 24 and 48 hours post transfection, filtered over a 0.22 µm GV filter (Millipore) and stored at ±80° C. Packaging of the HEK cDNA library was performed as described herein with the exception that $1.6 \times 10^7$ cells in a 175 cm² falcon were transfected with 87 µg pBG1-HEK293cDNA. For titer determination, 10% pMFG-EGFP (gift from Dr. Mulligan, Cambridge, Mass.) was included in the DNA in a parallel experiment. The virus titer was approximately $5 \times 10^6$ infectious units/ml as determined by FACS analysis of EGFP-expressing cells.

For infection with CIS "prey," target cells were seeded at a density of $2 \times 10^4$ cells/well in a 24-well plate and $10^6$ in 75 cm² culture flasks. The day after seeding, cells were incubated for 24-48 hours with supernatant containing virus and diluted in medium as described herein. Polybrene (Sigma) was added to a final concentration of 2.5 µg/ml. After infection, cells were stimulated with Epo (50 ng/ml) for 24-48 hours and followed by puromycin (1-2 µg/ml as described; Sigma) selection for ten days.

Construction of Bait, Prey and Reporter/Selector Constructs
Generation of the EpoR/LepR Chimera Polymerase chain reactions (PCR) were performed using Pfu polymerase (Stratagene, typically 2.5-5 U Pfu were used per reaction). The mouse leptin receptor (LepR) transmembrane and intracellular parts (amino acids 839-1162) were amplified by PCR using forward primer MBU-O-447 (SEQ ID NO:14 of the accompanying SEQUENCE LISTING, the entire contents of which are incorporated herein by this reference) that contains a PacI restriction enzyme recognition site and the reverse primer MBU-O-448 (SEQ ID NO:15) that contains a linker sequence (Gly-Gly-Ser) and a multicloning site (MCS) with SalI, SacI, SpeI, NotI and XbaI recognition sites. Only one amino acid from the extracellular part of the LepR was included in the fragment (Gly). Primer design resulted in the insertion of an Asn residue between the PacI generated Leu-Ile sequence and the extracellular Gly residue. The amplicon was gel-purified and ligated in the pCR® Blunt vector (Invitrogen Corporation, San Diego, Calif.). PacI-SacI digestion on the pCR® Blunt vector results in the desired LepR fragment after gel-purification.

The pSV-SPORT-EpoR/IFNaR2-2 (Pattyn et al., 1999) vector expresses an EpoR/IFNaR2-2 receptor chimera and was constructed as follows: RNA was isolated from $5 \times 10^6$ TF-1 cells using the RNeasy® kit (Qiagen GmbH Corporation, Milden, Federal Republic of Germany). RT-PCR was performed as follows: 2 (2 µg) of oligodT (12-18 mer; Pharmacia) was added and incubated at 70° C. for 10 minutes, the reaction mixture was chilled on ice for 1 minute, cDNA was prepared by adding 4 µl of 10×RT buffer (Life Sciences), 1 µl 20 mM dNTP's (Pharmacia), 2 µl 0.1 M DTT, and 1 µl of MMLV reverse transcriptase (200 U; Superscript RT; Life Technologies) to an end volume of 20 µl. Incubations were performed as follows: RT for 10 minutes, 42° C. for 50 minutes, 90° C. for 5 minutes, and 0° C. for 10 minutes. Following the incubations, 0.5 µl RnaseH (2 U; Life Technologies) was added and the mixture was incubated at 37° C. for 20 minutes, followed by chilling on ice.

PCR on the resulting cDNA was performed using Pfu enzyme (5 U; Stratagene). Forward primer MBU-O-167 (SEQ ID NO:7) and reverse primer MBU-O-308 (SEQ ID NO:10) were designed to amplify the extracellular part of the EpoR (amino acids 1-249) between a KpnI and PacI site. A band of correct size was purified and the DNA was digested with KpnI and PacI. The digested DNA was inserted into the KpnI-PacI opened pSV-SPORT-IL-5Rα/IFNaR2-2 vector. This vector contains a chimeric receptor that has the extracellular domain of the IL-5Rα receptor fused to the transmembrane and intracellular domains of IFNaR2-2. By site-specific mutagenesis, a PacI site was added to the fusion point by means of the Quikchange® site-directed mutagenesis kit (Stratagene Corporation, LaJolla, Calif.), which resulted in the insertion of two amino acids (Leu-Ile) before the most membrane-proximal, extracellular amino acid (Lys) of IFNaR2-2. Thus, using the KpnI site that precedes the coding sequence and the created PacI site on the extracellular/transmembrane domain fusion site, the extracellular domain of IL-5Rα could be exchanged by the one of EpoR, as described herein.

The LepR fragment generated by PacI-SacI digestion was ligated in the PacI-SacI-digested and gel-purified pSV-SPORT-EpoR/IFNaR2-2 vector, resulting in pSV-SPORT-EpoR/LepR.

Generation of IL-3Rα/LepR, IL-5Rα/LepR, GM-CSFRα/LepR and $\beta_c$/LepR Chimeras The pSV-SPORT-IL-5Rα/IFNaR2-2 and pSV-SPORT-$\beta_c$/IFNaR1 vectors express an IL-5Rα/IFNaR2-2 and a $\beta_c$/IFNaR1 chimera, respectively, including the extracellular portion of the IL-5Rα or $\beta_c$ chain, and the transmembrane and intracellular parts of the IFNaR2-2 or IFNaR1. A PacI site was used to generate the fusion site preceding the transmembrane segment. The IFNaR2-2 or IFNaR1 parts in these vectors were replaced by the same segments of the LepR using the PacI site and an XbaI site which is located just after the IFNaR2-2 or IFNaR1 stop codon. Thus, the LepR fragment was generated by a PacI-XbaI digest of the pSV-SPORT-EpoR/LepR vector (see example 1) and was inserted into the PacI-XbaI opened, gel-purified pSV-SPORT-IL-5Rα/IFNaR2-2 and pSV-SPORT-$\beta_c$/IFNaR1 vectors, resulting in the vectors pSV-SPORT-IL-5Rα/LepR and pSV-SPORT-$\beta_c$/LepR.

The pSV-SPORT-IL-3Rα/LepR and pSV-SPORT-GM-CSFRα/LepR vectors were constructed as follows: the extracellular portion of the IL-3Rα and GM-CSFRα chains were amplified using standard RT-PCR procedures with Pfu polymerase. Two µl TF-1 cDNA was used as input. Forward primers were MBU-O-752 (IL-3Rα) and MBU-O-754 (GM-CSFRα) and generated a KpnI site. Reverse primers MBU-O-753 (IL-3Rα) and MBU-O-755 (GM-CSFRα) contain a PacI site allowing in-frame fusion to the LepR. After subcloning in the pCR® Blunt vector (Invitrogen Corporation, San Diego, Calif.), the KpnI-PacI-excised extracellular fragments were ligated into the KpnI-PacI opened pSV-SPORT-IL-5Rα/LepR. For the GM-CSFRα construction, a partial KpnI digest was used since the extracellular portion contained an internal KpnI site. The resulting vectors, pSV-SPORT-IL-3Rα/LepR and pSV-SPORT-GM-CSFRα/LepR, contain chimeric receptors including the extracellular portion of the IL-3Rα or GM-CSFRα chain fused to the transmembrane and cytoplasmatic tail of the LepR.

Generation of the EpoR/LepR-F3 Chimera

The mutant leptin receptors (Eyckerman et al., 1999) Y985-1077F and Y985-1077-1138F (LepR-F3; previously called F-all) were generated using the Quikchange® site-directed mutagenesis procedure (Stratagene Corporation, LaJolla, Calif.) using Pfu polymerase on the pMET7-LepR template. Mutagenic oligonucleotides were MBU-O-157 (SEQ ID NO:1), MBU-O-158 (SEQ ID NO:2), MBU-O-159 (SEQ ID NO:3), MBU-O-160 (SEQ ID NO:4), MBU-O-161 (SEQ ID NO:5) and MBU-O-162 (SEQ ID NO:6). Each mutation was coupled to a change in restriction cleavage and confirmed by restriction and DNA sequence analysis. The double and triple mutants were created using a sequential approach. Signaling properties of the generated mutants were investigated at the gene induction level using the rPAP1-luci reporter construct (as described herein) and Northern blot analysis of induction of Metallothionein II gene transcripts. The double Y985-1077F mutant showed a higher stimulation of the relevant genes compared to the wild-type LepR, which is probably a result of loss of recruitment of an SH2-module containing tyrosine phosphatase, such as SHP-1 or SHP-2. The triple Y985-1077-1138F (LepR-F3) showed almost complete loss of induction due to elimination of the Box3 or STAT-3 association motif resulting in a receptor which allows phosphorylation and activation of the associated JAK2 kinase, but which cannot deliver a stimulatory signal to the studied genes.

PCR amplification on the pMET7-LepR-F3 vector template using MBU-O-447 (SEQ ID NO:14) and MBU-O-448 (SEQ ID NO:15) as forward and reverse primers, respectively, resulted in an LepR-F3 amplicon spanning the transmembrane and intracellular domains of LepR-F3 (+1 extra Gly of the extracellular part, see herein), which was subcloned in the pCR® Blunt vector (Invitrogen Corporation, San Diego, Calif.). PacI-SacI digestion of the resulting plasmid yielded a DNA fragment containing the LepR-F3 sequence which was ligated into a PacI-SacI-digested and gel-purified pSV-SPORT-EpoR/IFNaR2-2 vector (as described herein). This resulted in pSV-SPORT-EpoR/LepR-F3, which was renamed to pSEL1.

Generation of the Prey Vector

Prey constructs were generated in the pMET7 vector, which contains a strong constitutive hybrid SRα promoter (Takebe et al., 1988).

Through site-directed mutagenesis (using the QUIKCHANGE® site-directed mutagenesis procedure available from Stratagene Corporation, LaJolla, Calif.), a unique ApaI site was introduced after the pMET7 promoter and before the unique EcoRI site in the pMET7mcs vector, resulting in pMET7mcsA (primers MBU-O-567 (SEQ ID NO:24) and MBU-O-568 (SEQ ID NO:25)).

The pMET7mcs vector is a modified version of pMET7 containing an expanded MCS by insertion of the extra unique BglII, EcoRV, BstEII, AgeI and XhoI restriction sites. PCR amplification of the pSVL-gp130 template using the forward primer MBU-O-586 (SEQ ID NO:53) and the reverse primer MBU-O-443 (SEQ ID NO:11) generated a DNA fragment encoding a 158-amino acid-long intracellular fragment of the human gp130 chain, which contains four STAT-3 association motifs (amino acids 761-918, the stop codon was not co-amplified). The forward primer contains, from 5' to 3', an ApaI restriction site, a Kozak consensus sequence, a flag-tag encoding sequence (Met-Asp-Tyr-Lys-Asp-Asp-Asp-Asp-Lys-Ile) (SEQ ID NO:48) and a BglII restriction site. The reverse primer encodes an additional hinge sequence (Gly-Gly-Ser) and contains an EcoRI recognition site. ApaI and EcoRI digestion of the PCR product (after subcloning in pCR® Blunt, Invitrogen Corporation, San Diego, Calif.) and of pMET7-mcsA, allowed the gp130 fragment to be ligated into the pMET7 vector, generating the pMET7-flag-gp130 construct.

SV40 largeT antigen (SVT) was amplified using a vector from the HYBRIZAP®-2.1 Two-Hybrid cDNA synthesis kit (Stratagene Corporation, LaJolla, Calif., pSV40) as a template. Primers MBU-O-445 (SEQ ID NO:12) and MBU-O-446 (SEQ ID NO:13) were used to generate a DNA fragment encoding 448 amino acids between residues 261 and 708. The N-terminal deletion eliminates the nuclear targeting signal in SVT. The forward primer contains an EcoRI recognition site that allows in-frame ligation to the gp130-hinge sequence. The reverse primer contains additional NruI, XhoI, BglII, NotI and XbaI restriction sites and encodes the stop codon after the SVT coding sequence. Subcloning in pCR® Blunt (Invitrogen Corporation, San Diego, Calif.), followed by recovery of the cleaved amplicon with EcoRI and XbaI, allowed ligation in the EcoRI-XbaI opened pMET7-flag-gp130 vector, thus yielding pMET7-flag-gp130-SVT, which was renamed to pMG1-SVT. Digestion with EcoRI-XhoI or EcoRI-NotI allows the insertion of model preys or of cDNA libraries into this vector. In these cases, the SVT fragment acts as a "stuffer."

Construction of the p53-SVT Interaction Trap Vectors

A DNA fragment encompassing murine p53 was amplified with MBU-O-450 (SEQ ID NO:16) and MBU-O-451 (SEQ ID NO:17) using the p53 control plasmid from the HYBRIZAP®-2.1 Two-Hybrid cDNA synthesis kit (Stratagene Corporation, LaJolla, Calif.) as a template. The forward primer contains an SalI restriction site that allows in-frame coupling to the EpoR/LepR-F3 hinge construct. The reverse primer contains a STOP codon and an XbaI restriction site. The 243 amino acid-long p53 fragment (amino acids 73-315) contains the interaction site with SVT, but lacks the nuclear targeting signal and the oligomerization domain. Subcloning over pCR® Blunt (Invitrogen Corporation, San Diego, Calif.), digestion with SalI-XbaI and gel-purification yielded a fragment that was ligated into an SalI-XbaI cut, gel-purified pSEL1 vector, resulting in pSEL1-p53.

Generation of the pMG1-SVT Vector is as Described Herein

Amplification using MBU-O-695 (SEQ ID NO:31) and MBU-O-696 (SEQ ID NO:32) as forward and reverse primers, respectively, and using pMG1-SVT as a template resulted in an SVT fragment (amino acids 261-708+stop codon) between BglII and XbaI recognition sites. The BglII-XbaI-digested and purified PCR fragment was ligated into a BglII-XbaI cut and gel-purified pMG1-SVT vector, resulting in pMET7-SVT.

Construction of EpoR-CIS Interaction Trap Vectors

RNA was prepared from $5 \times 10^6$ TF-1 cells using the RNeasy® kit (Qiagen GmbH Corporation, Milden, Federal Republic of Germany) and eluted in 50 µl water from which 10 µl was used as input for RT-PCR. RT-PCR was performed using standard reaction conditions as described herein. An intracellular fragment of the human EpoR (amino acids 370-453) was amplified from 4 µl TF1 cDNA using MBU-O-675 (SEQ ID NO:27) and MBU-O-676 (SEQ ID NO:28) as forward and reverse primers, respectively, with two consecutive PCR reactions and an intermediate gel-purification. SacI and XbaI recognition sites are present in the forward and reverse primers, respectively. The reverse primer also encodes a stop codon. After gel-purification of the PCR amplicon band of the correct size, the fragment was subcloned in pCR® Blunt (Invitrogen Corporation, San Diego, Calif.), digested with SstI (which has the same recognition site as SacI) and XbaI, and ligated into an SstI-XbaI-digested, gel-purified pSEL1 vector, resulting in the pSEL1-EpoR construct.

Through site directed mutagenesis (using Quikchange® site directed mutagenesis procedure, Stratagene Corporation, LaJolla, Calif.), a Tyr to Phe mutation on position 426 in the human EpoR was introduced in the pSEL1-EpoR construct, resulting in an inactive EpoR fragment. Forward primer MBU-O-717 (SEQ ID NO:33) and reverse primer MBU-O-718 (SEQ ID NO:34) were used for the PCR-based mutagenesis, which also resulted in the insertion of an EcoRI enzyme recognition site. Introduction of the mutation was confirmed by restriction and DNA sequence analysis. The construct was named pSEL1-EpoRY-F.

The complete coding region for mouse Cytokine Inducible SH2-containing protein CIS (amino acids 2-257) was amplified using MBU-O-677 (SEQ ID NO:29) and MBU-O-678 (SEQ ID NO:30) as forward and reverse primers, respectively. The forward primer contains an EcoRI recognition site and the reverse primer contains an XbaI recognition site and the stop codon. The amplified, gel-purified fragment was subcloned into pCR® Blunt vector (Invitrogen Corporation, San Diego, Calif.). The insert was recovered by EcoRI and XbaI digestion, gel-purified and cloned into an EcoRI-XbaI-digested and gel-purified pMG1-SVT vector, leading to the pMG1-CIS vector.

Construction of the IRS1-Vav Interaction Trap Vectors

Through a mutagenesis approach (using Quikchange® site directed mutagenesis, Stratagene Corporation, LaJolla, Calif.), four amino acids ($P_{1137}$-Y-M-$P_{1140}$) within the mutant leptin receptor Y985-1077F (pMET7 LepR Y985-1077F) were exchanged for a phosphotyrosine-encoding region from human IRS1 (Insulin Receptor Substrate 1; $S_{892}$-P-G-E-Y-V-N-I-E-$F_{901}$) (SEQ ID NO:49). This removes the functional STAT3 association motif within the leptin receptor. Primers MBU-O-515 (SEQ ID NO:22) and MBU-O-516 (SEQ ID NO:23) were used for the PCR-based mutagenesis. The resulting construct was named pMET7 LepR-IRS1.

Using standard RT-PCR procedures with Pfu polymerase, full-size human GRB2 (Growth Receptor Bound 2; aa 1-217) was amplified using 2 µl HepG2 cDNA as input, and using MBU-O-467 (SEQ ID NO:18) and MBU-O-468 (SEQ ID NO:19) as forward and reverse primers, respectively. The forward primer contains an extra EcoRI site which allows in-frame fusion to the gp130 chain in the pMG1 vector and the reverse primer contains an extra XbaI site after the stop codon. After subcloning in the pCR® Blunt vector (Invitrogen Corporation, San Diego, Calif.), the EcoRI-XbaI excised fragment was ligated into the EcoRI-XbaI cut pMG1 vector, resulting in pMG1-GRB2. The SH2 domain of GRB2 (aa 60-158) was amplified in the same manner using primers MBU-O-469 (SEQ ID NO:20) and MBU-O-470 (SEQ ID NO:21) as forward and reverse primers, respectively. The forward primer contains an extra EcoRI recognition site which allows an in-frame fusion to the gp130 chain, and the reverse primer contains an extra stop codon and an XbaI enzyme recognition site. After subcloning of the PCR fragment in the pCR® Blunt vector (Invitrogen Corporation, San Diego, Calif.), the EcoRI-XbaI-generated fragment was ligated in the EcoRI-XbaI cut pMG1 vector, resulting in the pMG1-GRB2S vector.

A fragment of human GRB2 comprising the C-terminal SH3 domain (aa 159-217) was amplified using the pMG1-GRB2 construct as a template and MBU-O-770 (SEQ ID NO:38) and MBU-O-468 (SEQ ID NO:19) as forward and reverse primers, respectively. MBU-O-770 (SEQ ID NO:38) allows for an in-frame fusion to the flag tag by a BglII site and MBU-O-468 (SEQ ID NO:19) as described herein. After subcloning the PCR fragment in the pCR® Blunt vector (Invitrogen Corporation, San Diego, Calif.), the GRB2 fragment was inserted in the pMG1 vector by a BglII-XbaI-based exchange, resulting in the pMET7-GRB2SH3 vector.

A fragment of human Vav (VavS: aa 259-789) was amplified using Pfu polymerase from mRNA of the human TF1 cell line by standard RT-PCR techniques. Primers were MBU-O-737 (SEQ ID NO:35) and MBU-O-738 (SEQ ID NO:36) as forward and reverse primers, respectively. MBU-O-737 (SEQ ID NO:35) contains an extra EcoRI allowing for in-frame fusion to gp130, and MBU-O-738 (SEQ ID NO:36) contains a Stop codon and an XhoI enzyme recognition site. The amplified fragment was subcloned in the pCR® Blunt vector (Invitrogen Corporation, San Diego, Calif.) and ligated in the pMG1 vector through an EcoRI-XhoI-based exchange. The VavS fragment was also amplified using forward primer MBU-O-771 (SEQ ID NO:39), reverse primer MBU-O-741 (SEQ ID NO:37) and pMG1-VavS as a template. The forward primer contains a BamHI site which allows for an in-frame fusion to the flag tag, and the reverse primer contains a stop codon and an XbaI restriction site. The amplicon was subcloned in the pCR® Blunt vector (Invitrogen Corporation, San Diego, Calif.) and excised with BamHI and XbaI. The purified fragment was cloned in a BglII-XbaI cut pMG1 vector, resulting in the pMET7-VavS construct.

Construction of the pGL3-rPAP1-luci and pSEAP-rPAP1 Reporter Constructs

Genomic DNA was isolated from the rat pheochromocytoma PC12 cell line using the DNAzol procedure (Gibco-BRL, Gaithersburg, Md.). Optimal primers for PCR amplification of the rat PAP1 promoter were selected using a software program, such as the "Oligo Primer 3" program. Forward and reverse primers were MBU-O-222 (SEQ ID NO:8) and MBU-O-223 (SEQ ID NO:9), respectively. Amplification was performed using Taq polymerase in 30 cycles: 2 minutes at 94° C., 2 minutes at 57° C., 2 minutes at 72° C., followed by a 10-minute fill-in reaction at 72° C. Optimal $MgCl_2$ concentration was determined to be 6 mM. The promoter fragment was cloned after polishing with Klenow polymerase in the pCR® Blunt vector (Invitrogen Corporation, San Diego, Calif.). The promoter fragment was cut from the plasmid construct using a successive PstI digest, Klenow treated to polish the end, and BamHI digested, resulting in a blunt-sticky fragment. The gel-purified fragment was cloned into a SmaI-BglII opened, gel-purified pGL3 control vector (Promega). Digestion with SstI-SpeI restriction enzymes and gel-purification resulted in a fragment that was cloned into an SstI-NheI and purified pGL3 basic vector, resulting in the pGL3-rPAP1-luci construct. DNA sequencing revealed ten nucleotides differing from the published sequence, wherein the difference did not affect the leptin-dependent induction of the promoter segment.

The full-length rPAP1 promoter fragment was excised from pGL3 rPAP1-luci by partial digestion with KpnI and XhoI, and ligated into the KpnI-XhoI opened pXP2d2 vector (gift from Prof. S. Nordeen), resulting in pXP2d2-rPAP1-luci. The coding sequence for puromycin was amplified using primers MBU-O-719 (SEQ ID NO: 40) and MBU-O-720 (SEQ ID NO: 41) on the pIRESpuro2 template (Clontech, Palo Alto, Calif.). The amplified puromycin coding sequence was combined with XhoI-XbaI digestion which allowed insertion into the pXP2d2-rPAP1-luci construct, resulting in pXP2d2-rPAP1-puro$^R$.

Digestion of the pGL3-rPAP1-luci construct using MluI and XhoI restriction enzymes resulted in a fragment spanning the full size rPAP1 promoter. This fragment was gel-purified and ligated into an MluI-XhoI cut, gel-purified pSEAP vector (TROPIX, Perkin Elmer), resulting in the pSEAP-rPAP1 construct. Functionality of the pSEAP-rPAP1 construct was assayed by transient co-transfection of pMET7 LepR and pSEAP-rPAP1 in PC12 cells using the Phospha-Light™ secreted alkaline phosphatase reporter gene assay system (Applied Biosystems, Foster City, Calif.).

Construction of the pcDNA5/FRT-EpoR and pBG1-SVT, pBG1-CIS and pBG1-ccdB Vectors Insertion of the EpoR-LR-F3-EpoR into the pcDNA5/FRT vector was performed by re-amplifying the complete chimeric construct using MBU-O-167 (SEQ ID NO:7) and MBU-O-769 (SEQ ID NO: 43) on the pSEL1-EpoR template, followed by subcloning using KpnI and NotI sites. This construct was named pcDNA5/FRT-EpoR.

The SVT fragment was re-amplified from pMG1-SVT using forward primer MBU-O-766 (SEQ ID NO: 42) and MBU-O-446 (SEQ ID NO:13). BamHI-NotI digestion allowed insertion in the pBMN-Z retroviral vector (gift from G. Nolan), resulting in vector pBG1-SVT. EcoRI-NotI based exchange of the SVT fragment for CIS (pMG1-CIS) resulted in the pBG1-CIS vector.

To allow counter-selection for vector self-ligation in the case of insertion of cDNA libraries in the pBG1 vector, the *E. coli* control of cell death gene (ccdB) was amplified using primers MBU-O-835 (SEQ ID NO: 44), MBU-O-836 (SEQ ID NO:45), template pENTRY11 (Life Technologies, Gaithersburg, Md.) and cloned in the pBG1-CIS vector by an EcoRI-NotI restriction-based insertion, resulting in the pBG1-ccdB vector.

Construction of the Bait-modifying Enzyme, Substrate-bait and Prey Chimeras

Generation of the pSV-SPORT-GM-CSFRα/LepR-F3 and pSV-SPORT-β$_c$/LepR-F3 Chimeras The LepR fragment in pSV-SPORT-GM-CSFRα/LepR and pSV-SPORT-β$_c$/LepR was replaced by the LepR-F3 fragment of pSEL1 (pSV-SPORT-EpoR/LepR-F3) using the PacI and NotI site. Thus, the LepR-F3 fragment was generated by a PacI-NotI digest of the pSEL1 construct, gel-purified and inserted into the PacI-NotI opened and gel-purified pSV-SPORT-GM-CSFRα or pSV-SPORT-β$_c$ vectors, resulting in the vectors pSV-SPORT-GM-CSFRα/LepR-F3 or pSV-SPORT-β$_c$/LepR-F3.

Generation of the pSV-SPORT-GM-CSFRα/LepR-F3-modifying Enzyme Chimera and pSV-SPORT-β$_c$/LepR-F3-modifying Enzyme Chimera and Generation of the pSV-SPORT-GM-CSFRα/LepR-F3-bait Chimera and pSV-SPORT-β$_c$/LepR-F3-bait Chimera The pSV-SPORT-GM-CSFRα/LepR-F3 and pSV-SPORT-β$_c$/LepR-F3 vectors were digested with SalI, gel-purified and the ends were polished with Klenow fragment (Boehringer Mannheim). The blunt ended vectors were incubated with Alkaline Phosphatase (Boehringer Mannheim) to dephosphorylate the blunt ends. To produce the modifying enzyme, the mouse cytoplasmic tail of ALK4 (with mutation T206D) was placed in the vector pGBT9 (obtained from Prof. D. Huylebroeck), resulting in a constitutive active kinase. The mutated cytoplasmic tail of ALK4 was removed from the construct by an EcoRI-BamHI digestion, gel-purified and incubated with Klenow fragment to polish the ends. The insert was ligated in the opened pSV-SPORT-GM-CSFRα/LepR-F3 and pSV-SPORT-β$_c$/LepR-F3 vectors, resulting in pSV-SPORT-GM-CSFRα/LepR-F3-ALK4CA and pSV-SPORT-β$_c$/LepR-F3-ALK4CA, respectively.

To produce the bait, a construct containing a human cDNA encoding the entire Smad3 protein in vector pcdef was obtained as a kind gift of Prof. D. Huylebroeck. The Smad3 insert was removed with an EcoRI-XhoI digestion, gel-purified and the ends were polished by Klenow fragment (Boehringer Mannheim). The Smad3 insert was ligated into the opened pSV-SPORT-GM-CSFRα/LepR-F3 and pSV-SPORT-β$_c$/LepR-F3 vectors (as described herein) resulting in pSV-SPORT-GM-CSFRα/LepR-F3-Smad3 and pSV-SPORT-β$_c$/LepR-F3-Smad3.

Generation of the pMG2-prey Chimera

For construction of the pMG2 vector, the pMG1-SVT vector was digested with EcoRI and NotI and incubated with Klenow fragment (Boehringer Mannheim) to polish the ends. The blunt ended vector was incubated with Alkaline Phosphatase (Boehringer Mannheim) to dephosphorylate the blunt ends. Cassette dB of the Gateway Vector Conversion System (Life Technologies) was ligated into the opened vector leading to the pMG1-gateway vector. A PCR reaction using primers MBU-O-1094 (SEQ ID NO:46) and MBU-O-1076 (SEQ ID NO:47) on the pMG1-SVT template was performed, resulting in a fragment containing gateway recombination sites and a part (amino acids 905-918) of the gp130 chain. The fragment was cloned in the pMG1-gateway vector using a two-step gateway reaction (Life Technologies), resulting in pMG2-SVT, which is a prey construct with a total of six STAT recruitment sites. The pMG2-SVT construct was digested by EcoRI-XhoI and gel-purified. For the prey, a construct obtained from Prof. D. Huylebroeck contained a cDNA encoding almost the entire human Smad4 protein, only lacking the first three amino acids. The Smad4 insert was removed by an EcoRI-XhoI digestion, gel-purified and ligated into the opened pMG2 vector.

Construction of the Reporter Cell Lines

Selection of the Hek293T PAP21 Reporter Cell Line

The Blasticidin system (Invitrogen Corporation, San Diego, Calif.) was used to create a stable cell line with an endogenous pSEAP-rPAP1 reporter construct. Sensitivity to the toxic agent Blasticidin (Invitrogen Corporation) of Hek293T cells was estimated to be 3 µg/ml. Ten$^6$ cells were seeded in a Petri dish and transfected the day after seeding using the Calcium Phosphate Transfection System (Life Technologies) according to the manufacturer's instructions. A total of 20 µg DNA was transfected (18 µg of pSEAP-rPAP1seap and 2 µg of pcDNA6/V5-HisA, which contains a Blasticidin resistance gene). After 48 hours, the transfected cells were seeded in 96-well plates at ten cells per well. After 24 hours, Blasticidin was added at a concentration of 3 µg/ml and the cells were maintained under selective conditions for 3-4 weeks. The resulting single cell clones were screened by stimulation for 24 hours with 20 ng/ml hyper-IL6 (fusion protein of IL-6 with its specific receptor IL6-Rα; Fischer et al., 1997). Hek293T PAP21 was selected as the responsive cell line.

Generation of the HEK293-16 Cell Line

Flp-In-293 cells (Invitrogen Corporation) were stably transfected with a plasmid containing expression cassettes for the mouse ecotropic retroviral receptor (mEcoR) and for neomycin resistance. The pool of neomycin-resistant cells (resistant to 400 µg/ml geneticin, Life Technologies) was super-transfected at a ratio of 5:1, respectively, with the following two plasmids: i) a plasmid carrying the cDNA encoding the puromycin resistance marker (puromycin-N-acetyl-transferase) under control of promoter sequences of rPAP1 (pXP2d2-rPAP1-puro$^R$), and ii) a plasmid carrying the cDNA for the blasticidin resistance marker (blasticidin S deaminase) under the control of the EM7 promoter (pcDNA6/V5-His, Invitrogen Corporation). After selection in blasticidin S (5 µg/ml, Invitrogen), single colonies were picked and seeded in 24-well plates. Puromycin resistance (1 µg/ml, Sigma; added 48 hours after seeding) was monitored in the absence or presence of LIF (1 ng/ml). After another five days, surviving cells were stained with crystal violet using a standard procedure.

RT-PCR Analysis

Cells were lysed in 100 µl RLT buffer (RNeasy® method, Qiagen GmbH Corporation) and chromosomal DNA was sheared using Qiashredder columns (Qiagen GmbH Corporation). Beads were pretreated according to the manufacturers' instructions (Dynabeads M-280 Streptavidin, Dynal). Dynabeads were washed twice in a high salt buffer (1 M NaCl, 10 mM Tris HCl pH 7.5 and 1 mM EDTA) and incubated with 200 pmoles of biotinylated oligonucleotide directed against the gp130 chain (5' GGGCTGGGTA-GACTCGGATCTTGAGAAGAC) (SEQ ID NO:50). Next, beads were washed three times in the high salt buffer and resuspended in a low salt buffer (0.15 M NaCl, 10 mM Tris HCl pH 7.5 and 1 mM EDTA) to a concentration of 10 µg/µl. Five µl of this suspension was added to 100 µl total lysate diluted 1/5 in the high salt buffer. Fifteen minutes after gentle rotation at room temperature, the beads were washed three times with low salt buffer and eluted in 30 µl water for 2 minutes at 65° C. Fifteen µl of this sample was used as input for a standard RT-PCR reaction with the Qiagen OneStep RT-PCR Kit (Qiagen GmbH Corporation). Primers 5' GGCATGGAGGCTGCGACTG (SEQ ID NO:51) and 5' TCGTCGACCACT GTGCTGGC (SEQ ID NO:52) were used for amplification of the "prey" fragment. In a pilot experiment using CIS as a "prey" template, efficient amplification was obtained with lysate from less than $10^3$ cells.

Reporter Assays, Binding Assays, Cell Survival Assay and FACS Analysis

Luciferase was measured after lysis of the cells and addition of the luciferase substrate, Luciferin (Duchefa Biochemie, B.V.). Light emission was measured using a TopCount chemiluminescence counter (Canberra Packard). All luciferase measurements were normalized using an expression construct constitutively expressing β-galactosidase (pUT651), which was measured in triplicate for every transfection using the Galact-Star™ kit (Applied Biosystems).

Puromycin-resistant cell colonies were stained with crystal violet using a standard procedure.

Human erythropoietin receptor expression was monitored using goat anti-human EpoR polyclonal IgG (R&D Systems) at 2 µg/ml and Alexa 488-conjugated donkey anti-goat IgG (Molecular Probes) at 4 µg/ml. For demonstration of the expression of the FLAG-tagged "prey" construct, cells were fixed and permeabilized with the Starfiqs™ solution according to the manufacturer's protocol (Immuno Quality Products), stained with an anti-FLAG mouse mAb (Sigma) at 8 µg/ml and fluorescein-conjugated sheep anti-mouse IgG (Amersham), 1/50 diluted. All FACS analyses were performed on a BD FACSCalibur™ System (Becton Dickinson).

Generation of Retroviral cDNA Libraries and Screening Conditions

Construction of the HEK293 library was performed using standard procedures. Five µg of HEK293 polyA+mRNA was used as input for both oligo-dT and random primed first strand synthesis with Superscript II reverse transcriptase (Life Technologies). Both the oligo-dT and random primers contain an NotI site. After second strand synthesis, adaptors containing an EcoRI site were ligated. The cDNA was analyzed using agarose gel electrophoresis and fragments between 0.5 and 2.5 Kbp were cloned unidirectionally in the pBG1-ccdB vector opened with EcoRI-NotI.

For screening, a total of $6 \times 10^7$ "bait" expressing cells were seeded at a density of $2 \times 10^6$ per 175 $cm^2$ tissue culture flasks. Twenty-four hours after seeding, cells were infected with the retroviral HEK293 "prey" cDNA library (complexity of $2 \times 10^6$) for another 24 hours. After infection, cells were stimulated for 6.5 hours with 50 ng/ml Epo and puromycin was added at a final concentration of 2 µg/ml for 20 days. Single cell colonies were picked and analyzed using a functional assay and RT-PCR sequencing.

Immunoprecipitations and Western Blot Analysis

For demonstration of EpoR "bait" phosphorylation, approximately $3 \times 10^6$ HEK293T cells were transiently transfected with plasmids encoding the EpoR "bait" or the EpoR "bait" Y402F mutant and the CIS/SOCS-2 "preys." Cleared lysates (in modified RIPA buffer: 50 mM TrisHCl pH 8.0; 200 mM NaCl; 1% NP40; 0.5% DOC; 0.05% SDS; 2 mM EDTA; 1 mM $Na_3VO_4$; 1 mM NaF; 20 mM β-glycerophosphate; Complete™ protease inhibitor cocktail (Roche)) of stimulated and unstimulated cells were incubated with 2 µg goat anti-human EpoR polyclonal IgG and Protein G Sepharose (Amersham Pharmacia Biotech). After precipitation, polyacrylamide gel electrophoresis and blotting, phosphorylation was revealed using PY20 antibody (Transduction Laboratories).

Immunoprecipitation of "preys" was performed after transfection of EpoR/EpoRF "baits" and the SOCS-2 "prey" in HEK293T cells. Incubation of cleared lysates (modified RIPA) with anti-FLAG M2 affinity gel allowed SOCS-2 "prey" precipitation. Phosphorylation of the "prey" was revealed using the PY20 antibody. "Prey" expression levels were verified after stripping the blots and reprobing with anti-FLAG antibody.

STAT3 phosphorylation was demonstrated using the Phospho-STAT3 (Tyr705) Antibody (Cell Signaling) according to the manufacturer's instructions. STAT3 expression was verified on the same blots using anti-STAT3 antibody (Transduction Laboratories).

Example 1

Functionality of EpoR-LepR Chimera in the Hek293T PAP21 Cell Line

To determine the functionality of the EpoR/LepR chimera, three combinations of plasmids were transfected into Hek293T PAP21 cells:
(a) pSV-SPORT+pMET7mcs+pGL3-rPAP1-luci+ pUT651;
(b) pSV-SPORT EpoR/LepR+pMET7mcs+pGL3-rPAP1-luci+pUT651; and
(c) pMET7 LepRY985/1077F+pMET7mcs+pGL3-rPAP1-luci+pUT651.

Transfection was performed according to the calcium phosphate method (Graham and van der Eb, 1973). A precipitate was formed using 3.4 µg as total DNA input (0.4 µg for pUT651, 1 µg for each of the others) into a 300 µl total mixture. Two hundred µl of this mixture was added to $4 \times 10^5$ Hek293T PAP21 cells seeded the day before transfection into a six well plate (Falcon). Six hours after adding the mixture, the cells were washed once with Dulbecco's PBS (Life Technologies) and new DMEM medium (Life Technologies) was added. Two days after transfection, medium was removed and cells were resuspended using 200 µl Cell Dissociation Agent (Life Technologies). After neutralization with 1200 µl DMEM medium, 50 of the cell suspension was seeded into a 96-well plate (Costar) in triplicate for each condition and stimulated by adding recombinant human leptin (R&D systems) to a final concentration of 100 ng/ml, recombinant human erythropoietin (R&D systems) to a final concentration of 0.5 units/ml, the combination of leptin (same concentration as described herein) plus forskolin (Sigma, 10 µM final concentration) or the combination of erythropoietin (same concentration as described herein) plus forskolin (same concentration as described herein). A non-stimulated negative control was also incorporated in the experiment. Forskolin is a chemical agent that activates the adenylate cyclase present within the cells and leads to heightened levels of the second messenger cAMP.

Figure 1:
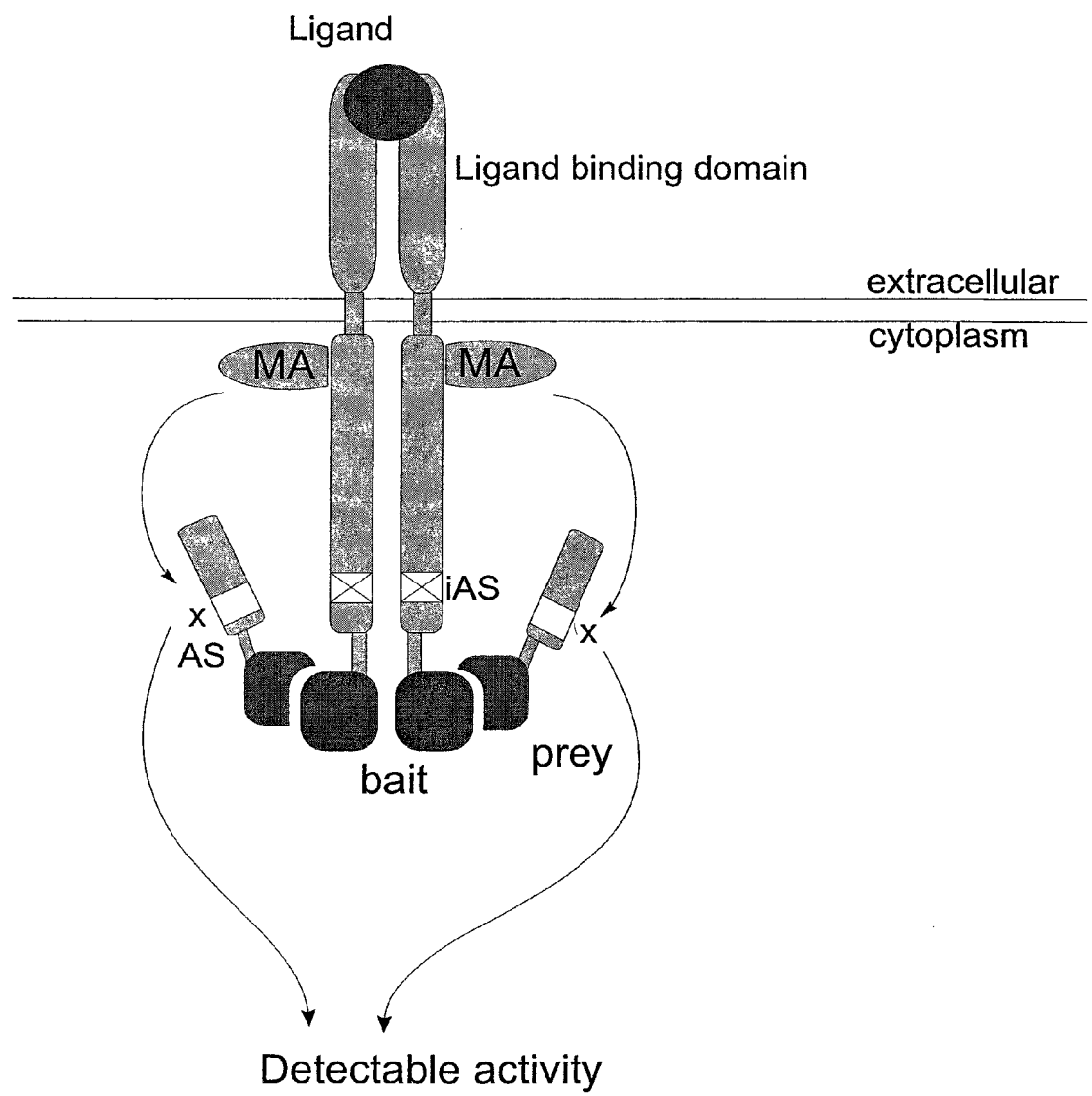
FIG. 1: Principle of the receptor-based interaction trap. Ligand binding activates a modifying enzyme activity (MA). Due to the inactivation of the normal receptor activation site (also referred to as "inactivated activation site" or "iAS"), the activation of modifying enzyme activity does not result in an activation of the signaling pathway unless the heterologous bait in the cytoplasmic domain of the recombinant receptor (referred to as "bait" in the drawing) binds to a prey polypeptide (referred to as "prey" in the drawing) which is fused to a polypeptide including an activation site (AS). The modifying enzyme activity may modify the activation site; modification (x) of the activation site results in activation of the signaling pathway and induction of a reporter system (referred to as "detectable activity" in the drawing).
Figure 2:
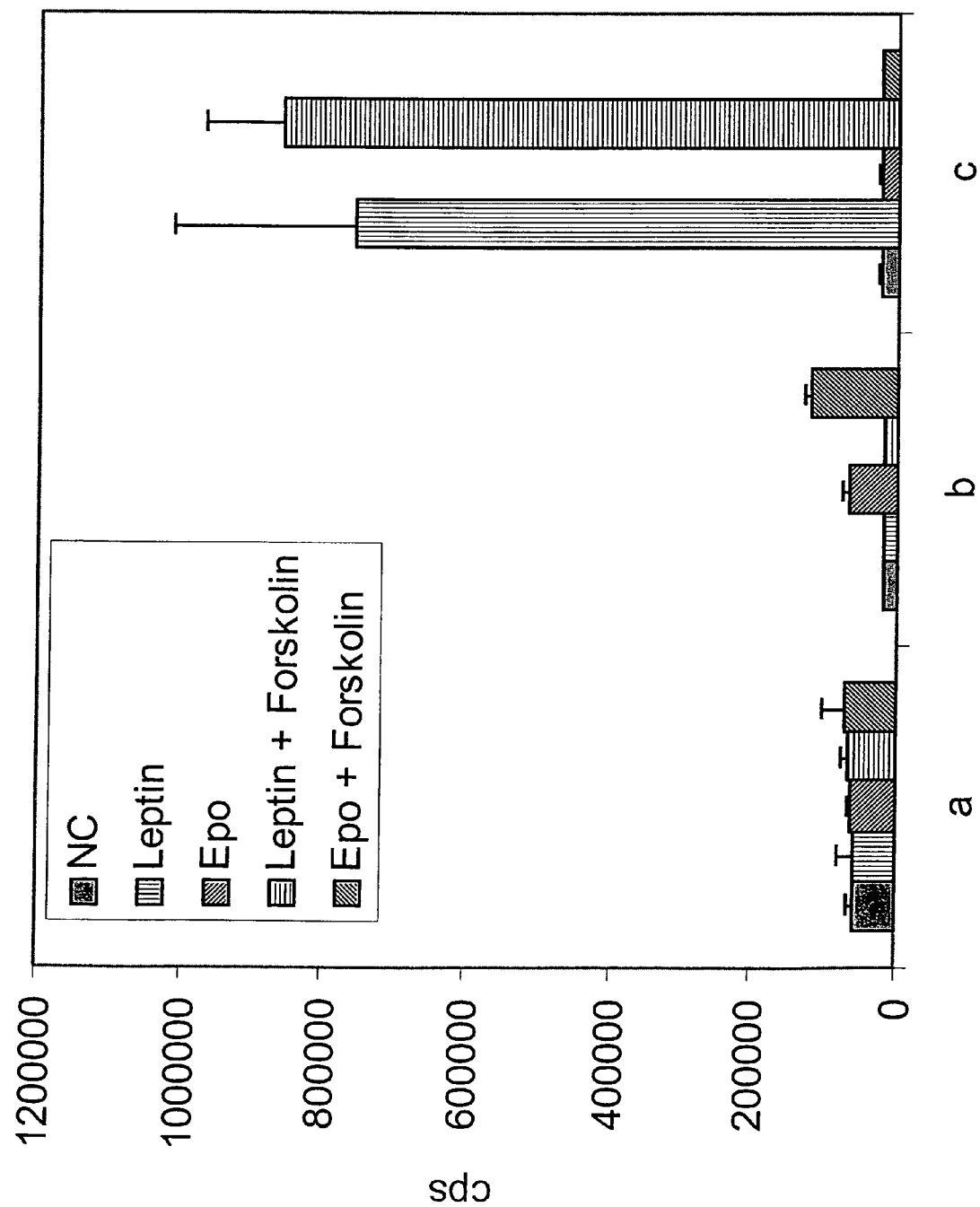
FIG. 2: Functionality of EpoR-LepR chimera in the Hek293T PAP21 cell line measured by luciferase light emission in a chemiluminescence counter (counts per second, cps). The cells were transfected with:
   (a)        pSV-SPORT+pMET7mcs+pGL3-rPAP1-luci+pUT651;
   (b) pSV-SPORT EpoR/LepR+pMET7mcs+pGL3-rPAP1-luci+pUT651; and
   (c)    pMET7 LepRY985/1077F+pMET7mcs+pGL3-rPAP1-luci+pUT651.

Treatment of transfected cells with forskolin alone did not result in a significant induction of luciferase activity. Through an undefined mechanism, cAMP elevation leads to strong co-stimulation with the leptin signal on PAP1 induction (Eyckerman et al., 1999). Twenty-four hours after stimulation, the cells were lysed in the wells and the luciferase substrate Luciferin (Duchefa) was added. Light emission was measured using a TopCount chemiluminescence counter (Canberra Packard). The mock control transfection (transfection a) showed no signal in all cases. Results are shown in FIG. 2. The transfection with the EpoR/LepR chimera resulted in a 3.7-fold induction with erythropoietin and a 6.5-fold induction with erythropoietin and forskolin. No significant signal was detected when stimulated with leptin or with leptin+forskolin. In the cells transfected with the LepR Y985/1077F mutant, a 33.2-fold induction was detected when stimulated with leptin and a 37.6-fold induction was detected when co-stimulated with forskolin. No signal was detected in both erythropoietin and erythropoietin+forskolin stimulated cells. All results were normalized using the internal transfection control vector pUT651 and the Galacto-Star™ kit (Applied Biosystems) (as described herein).

The difference in induction between EpoR/LepR and LepR Y985/1077F is likely due to the elimination in the latter receptor construct of tyrosines involved in the recruitment of tyrosine phosphatases and SOCS proteins to the complex, leading to an enhanced signal (Eyckerman et al., 1999).

Example 2

Functionality of p53-SV40 LargeT Interaction Trap

To investigate the functionality of the modification-independent interaction, the following plasmid combinations were transfected into 4×10⁵ Hek293T cells seeded in a six-well plate the day before transfection:
  (a)    pSV-SPORT+pMG1-SVT+pGL3-rPAP1-luci+ pUT651;
  (b)    pSV-SPORT+pMG1-CIS+pGL3-rPAP1-luci+ pUT651;
  (c)    pSV-SPORT+pMET7-SVT+pGL3-rPAP1-luci+ pUT651;
  (d)    pSEL1-p53+pMG1-SVT+pGL3-rPAP1-luci+ pUT651;
  (e) pSEL1-p53+pMG1-CIS+pGL3-rPAP1-luci+pUT651; and
  (f)    pSEL1-p53+pMET7-SVT+pGL3-rPAP1-luci+ pUT651.

A 300 µl precipitation mixture was prepared which contained 3.1 µg DNA (0.1 µg of pUT651, 1 µg of each of the others). Two hundred µl was added to the cells for 6 hours followed by washing once with Dulbecco's PBS. After washing, DMEM medium was added to the cells. After 24 hours, the cells were resuspended with 200 µl Cell Dissociation Agent and neutralized with 2,200 µl DMEM medium. Forty µl of the cell suspension was placed into a 96-well plate for each transfection and stimulated in triplicate. Sixty µl DMEM was added to obtain an end volume of 100 µl and after 24 hours, the cells were stimulated for 24 hours with erythropoietin or erythropoietin plus forskolin (same concentrations as described herein). A non-stimulated negative control was also included in the experiment. Luciferase measurements are shown in FIG. 3.

Transfected cells from transfections a, b and c showed no significant induction of the reporter construct under all conditions tested. A 9.4-fold induction and a 14.6-fold induction was detected in transfected cells from transfection d after stimulation with erythropoietin and erythropoietin plus forskolin, respectively, implying an interaction-dependent signal. No signal was detected in transfection e and f. This implies a specific interaction which leads to gp 130-dependent STAT-3 activation. All results were normalized using the internal transfection control vector pUT651 and the Galacto-Star™ kit (Applied Biosystems) as described herein.

Example 3

Functionality of the EpoR-CIS Phosphorylation-Dependent Interaction Trap

To determine the functionality of the EpoR-CIS phosphorylation-dependent interaction trap, the following plasmid combinations were transfected in 4×10⁵ Hek293T cells seeded the day before transfection:
  (a)    pSV-SPORT+pMG1-CIS+pGL3-rPAP1-luci+ pUT651;
  (b)    pSV-SPORT+pMG1-SVT+pGL3-rPAP1-luci+ pUT651;
  (c) pSV-SPORT+pEF-FLAG-I/mCIS+pGL3-rPAP1-luci+ pUT651;
  (d)    pSEL1-EpoR+pMG1-CIS+pGL3-rPAP1-luci+ pUT651;
  (e)    pSEL1-EpoR+pEF-FLAG-I/mCIS+pGL3-rPAP1-luci+pUT651;
  (f)    pSEL1-EpoRY-F+pMG1-CIS+pGL3-rPAP1-luci+ pUT651; and
  (g)    pSEL1-EpoR+pMG1-SVT+pGL3-rPAP1-luci+ pUT651.

A precipitation mixture of 300 µl containing 3.1 µg DNA (0.1 µg of pUT651, 1 µg of each of the others) was prepared. Two hundred µl of this mixture was applied to the cells. After 6 hours, the cells were washed once with Dulbecco's PBS and DMEM medium was subsequently added. After 48 hours, the cells were resuspended with 250 µl Cell Dissociation Agent. After neutralization with 2,200 µl DMEM medium, 100 µl of this cell suspension was placed into a 96-well plate (Costar). The cells were stimulated with erythropoietin or erythropoietin plus forskolin (for final concentrations) as described herein. A non-stimulated negative control was also included in the experiment. Luciferase expression was measured 24 hours after stimulation using a TopCount chemiluminescence counter (Canberra Packard). Transfected cells from transfections a, b, c, e, f and g showed no significant induction of luciferase activity. Transfected cells from transfection d showed a 6.2-fold and a 10.5-fold induction with erythropoietin or erythropoietin plus forskolin, respectively. This indicates an erythropoietin-dependent phosphorylation of the EpoR bait, thus resulting in interaction between the CIS protein and EpoR. Interaction leads to gp130 phosphorylation, STAT activation and signaling toward the rPAP1 promoter, thus leading to luciferase activity (FIG. 4).

Example 4

Functionality of the IRS1-GRB2-Vav Indirect Interaction Trap

To investigate the IRS1-GRB2-Vav indirect interaction trap, the following combinations of plasmids were transfected in 4×10⁵ Hek293T cells seeded the day before transfection:
  (a) pMET7mcs+pMG1-CIS+pGL3-rPAP1-luci+pUT651;
  (b)    pMET7mcs+pMG1-GRB2S+pGL3-rPAP1-luci+ pUT651;
  (c)    pMET7mcs+pMG1-VavS+pGL3-rPAP1-luci+ pUT651;
  (d) pMET7 LepR-IRS1+pMG1-CIS+pGL3-rPAP1-luci+ pUT651;

(e) pMET7 LepR-IRS1+pMG1-GRB2S+pGL3-rPAP1-luci+pUT651; and (f) pMET7 LepR-IRS1+pMG1-VavS+pGL3-rPAP1-luci+pUT651.

A 300 µl precipitation mixture was prepared containing 3.05 µg DNA (0.05 µg for pUT651, 1 µg for others). Two hundred µl of the mixture was added to the cells for 16 hours. After transfection, the cells were washed once with Dulbecco's PBS and DMEM was added (Gibco BRL). After 48 hours, the cells were resuspended in 200 µl of Cell Dissociation Agent (Gibco BRL) and neutralized by 1.8 ml DMEM medium. One hundred µl of cell suspension was seeded in a Costar 96-well plate and stimulated in a final volume of 200 µl with final concentrations of 100 ng/ml leptin, 100 ng/ml leptin plus 10 µM forskolin, 10 µM forskolin, or left unstimulated. Twenty-four hours after stimulation, luciferase and galactosidase activity assays were performed as described herein. From the results (FIG. 5), it can be concluded that the cells from transfections a, b, c, and d showed no significant induction of the rPAP1 promoter. Cells from transfection e show a slight induction with leptin and a moderate induction when co-stimulated with forskolin (2.5-fold), suggesting a direct interaction between IRS-1 and GRB2S. Transfection experiment f shows a clear induction of luciferase activity with leptin (5.2-fold) which is more pronounced when co-stimulated with forskolin (12.0-fold). This indicates an interaction between IRS1 and Vav which is probably mediated through endogenous GRB2.

To investigate the specificity and involvement of GRB2 in the interaction, and to test if the signal is generated by recruitment of the gp130 chain, a number of control experiments were performed.

The following combinations of plasmids were tested in the same way as described herein:

(a) pMET7 LepR-IRS1+200 ng pMG1-VavS+pGL3-rPAP1-luci+pUT651;

(b) pMET7 LepR-IRS1+200 ng pMG1-VavS+200 ng pMET7 GRB2SH3+pGL3-rPAP1-luci+pUT651; and (c) pMET7 LepR-IRS1+200 ng pMG1-VavS+1000 ng pMET7 GRB2SH3+pGL3-rPAP1-luci+pUT651.

Five-hundredths µg of pUT651 DNA and 1 µg of pMET7 LepR-IRS1 and pGL3-rPAP1-luci were added to the 300 µl precipitation mixture. The results (FIG. 6) are shown in fold induction. The results show a dose-dependent inhibition of rPAP1 induction when GRB2SH3 is overexpressed. Due to competition with endogenous GRB2 for Vav binding, recruitment of the 130-VavS fusion protein to the complex is blocked, resulting in a dose-dependent reduction of rPAP1 promoter activation. From this, it can be concluded that the specific GRB2-VavS interaction is required for induction of luciferase activity.

In order to investigate the critical role of gp130 recruitment in rPAP1 promoter induction, the following combinations of plasmids were transfected as described herein:

(a) pMET7 LepR-IRS1+200 ng pMG1-VavS+pGL3-rPAP1-luci+pUT651;

(b) pMET7 LepR-IRS1+200 ng pMG1-VavS+200 ng pMET7 VavS+pGL3-rPAP1-luci+pUT651; and (c) pMET7 LepR-IRS1+200 ng pMG1-VavS+1000 ng pMET7 VavS+pGL3-rPAP1-luci+pUT651.

The 300 µl precipitation mixture also contained 0.05 µg of pUT651 DNA, 1 µg of pMET7 LepR-IRS1 and pGL3-rPAP1-luci DNA. From the normalized results (FIG. 7), it can be concluded that gp130 in the gp130-VavS fusion construct is essential for PAP1 promoter induction since dose-dependent competition with uncoupled VavS leads to a significant reduction in luciferase activity.

Example 5

Optimalization of the Method for Library Screening

To permit easy interaction-dependent cDNA library screening, a selection system was developed as outlined in FIG. 8. An HEK293 cell clone was used (i) containing an FRT integration cassette in a transcriptionally active locus (Flp-In-293 cell line, Invitrogen Corporation), (ii) stably expressing the murine ecotropic retroviral receptor EcoR, and (iii) with a stably integrated pXP2d2-rPAP1-puro$^R$ selection cassette that directs STAT-regulated expression of the puromycin resistance gene. Clone HEK293-16 showed high sensitivity to puromycin (1 µg/ml), but acquired puromycin resistance upon LIF (Leukemia Inhibitory Factor)-induced activation of endogenous gp130 (FIG. 9A).

A model screening experiment involved the following successive steps: (i) EpoR "bait" expression was obtained after Flp recombinase-assisted integration of the pcDNA5/FRT-EpoR "bait" vector. Isogenic cells were selected by growth in hygromycin-containing medium (100 µg/ml, for ten days) and FACS analysis using anti-EpoR antibodies indicated that almost the whole cell population showed homogeneous expression of the chimeric "bait" receptor (FIG. 9B); (ii) Hygromycin-resistant cells were subsequently infected with CIS "prey"-expressing retrovirus for 24-48 hours wherein the retroviral gene transfer was chosen to attain expression from single integrants (Kitamura et al., 1995; Kojima and Kitamura, 1999); and (iii) cells were treated with Epo (50 ng/ml) for another 24-48 hours prior to puromycin selection.

As shown in FIG. 9C, colony formation was observed in Epo-stimulated HEK293-16 cells co-expressing EpoR-"bait" and gp130-CIS "prey" proteins. FACS analysis with anti-FLAG antibody of permeabilized, puromycin-resistant cells confirmed expression of the "prey" polypeptide (FIG. 9D). Rapid identification of expressed "prey" transcripts was performed using a RT-PCR procedure. Taking advantage of the fact that all "prey" polypeptides are fused to human gp130, a biotinylated, gp130-specific primer was used to select "prey" transcripts directly from cell lysates using streptavidin-magnetobeads. After reverse transcription, selective PCR amplification of the "prey" insert was obtained using a gp130/3'LTR primer pair. DNA sequence analysis of the amplicons recovered from Epo-stimulated, puromycin-resistant cells showed that transcripts encoding the 130-CIS "prey" were expressed as expected (FIG. 9D, inset).

FIG. 9E shows the results of a "spiking" experiment where a complex retroviral HEK293 cDNA library was mixed with a dilution series of retrovirus expressing the gp130-CIS "prey." A dose-dependent recovery of cell clones was observed in the presence of a ligand. RT-PCR cycle sequencing in a parallel experiment allowed identification of gp130-CIS "prey" expression in 19 of 21 clones analyzed.

Example 6

Library Screening with the MAPPIT System

A screening experiment with the EpoR "bait" using a retroviral HEK293 cDNA library (2×10$^6$ independent clones) was performed. To favor single integrants, 6×10$^7$ HEK293-16 cells expressing the EpoR "bait" were infected with an estimated infection efficiency of 4%. Three weeks after Epo stimulation and selection in medium containing 2 µg/ml puromycin, 33 colonies were picked and analyzed in a functional assay (FIG. 9F). Since all clones stably co-express "bait" and "prey," a specific interaction was demonstrated with the EpoR "bait" by co-transfection with the LR-F3, lacking the "bait," and the rPAP1-luciferase constructs. Three clones showed induction by Epo, but not by leptin, which indicated that the interaction occurred specifically with the Y402 EpoR motif. In one of these clones, RT-PCR analysis indicated the presence of a specific 1700 base amplicon and cycle sequencing revealed this fragment to encode SOCS-2, another member of the SOCS family. The latter was fused in frame within its pre-SH2 domain to gp130 (FIG. 9F), which underscores the low background observed with the two-hybrid procedure. After subcloning in a plasmid vector, ligand-dependent phosphorylation of SOCS-2 "prey" and of STAT3 was shown to depend on the phosphorylation of the Y402 EpoR motif (FIG. 9G). This demonstrates each of the phosphorylation (and interaction) steps preceding reporter gene activation.

Example 7

The Use of MAPPIT with Heterodimeric Receptors: Functionality of IL3R-, IL5R- and GM-CSFR-LepR Chimeras in the Hek 293T Cell Line In order to compare the functionality of the Epo, IL-3R, IL-5R and GM-CSFR LepR-chimera, the following combinations of plasmids were transfected into $4 \times 10^5$ Hek293T cells seeded the day before transfection:
    (a)    pSV-SPORT-EpoR/LepR+pGL3-rPAP1-luci+ pUT651;
    (b)  pSV-SPORT-IL-3Rα/LepR+pSV-SPORT-β$_c$/LepR+ pGL3-rPAP1-luci+pUT651;
    (c)  pSV-SPORT-IL-5Rα/LepR+pSV-SPORT-β$_c$/LepR+ pGL3-rPAP1-luci+pUT651;
    (d) pSV-SPORT-GM-CSFRα/LepR pSV-SPORT-β$_c$/LepR pGL3-rPAP1-luci+pUT651;
    (e)    pSV-SPORT-IL-3Rα/LepR+pGL3-rPAP1-luci+ pUT651;
    (f)    pSV-SPORT-IL-5Rα/LepR+pGL3-rPAP1-luci+ pUT651;
    (g)  pSV-SPORT-GM-CSFRα/LepR+pGL3-rPAP1-luci+ pUT651; and
    (h) pSV-SPORT-β$_c$/LepR+pGL3-rPAP1-luci+pUT651.

A 300 µl precipitation mixture was prepared as described herein which further contained 0.05 µg of pUT651 and 1 µg of each of the others vectors. Two hundred pl of this mixture was applied to the cells. After 6 hours, the cells were washed once with Dulbecco's PBS. After two days, the cells were resuspended in Cell Dissociation Agent and transferred to a 96-well plate (Costar). Transfections a-g were stimulated with 10,000, 1,000, 100, or 10 pg/ml of the respective cytokine. Cells of transfection h, expressing only the pSV-SPORT-β$_c$/LepR, were treated with 10 ng/ml Epo, IL-3, IL-5 or GM-CSF. A non-stimulated negative control was also included in the experiment. Luciferase expression was measured 24 hours after stimulation.

Results are given in FIG. 10. The EpoR/LepR chimera and a combination of IL-3Rα/LepR with β$_c$/LepR have similar fold inductions. A signal above background is observed at cytokine concentrations of 1 ng/ml. The biological activity of IL-5 on cells transfected with the chimera IL-5Rα/LepR and β$_c$/LepR is less than those for IL-3 or Epo. Cells transfected with chimeras of the GM-CSFR and the LepR are more sensitive to stimulation with a clear 7.7-fold induction at a concentration as low as 10 pg/ml. The cells from the negative controls, e.g., transfections e, f, g and h, showed no significant induction of luciferase activity.

Example 8

Functionality of the Smad3-Smad4 Phosphorylation-Dependent Interaction Trap

To determine the functionality of the Smad3-Smad4 phosphorylation-dependent interaction trap, the following plasmid combinations were transfected in $4 \times 10^5$ Hek293T cells seeded the day before transfection:
    (a)    pSV-SPORT-β$_c$/LepR-F3-ALK4CA+pSV-SPORT-GM-CSFRα/LepR-F3-Smad3+pMG2-Smad4+ pXP2d2-rPAP1-luci+pUT651;
    (b)  pSV-SPORT-βhd c/LepR-F3-Smad3+pSV-SPORT-GM-CSFRα/LepR-F3-ALK4CA+pMG2-Smad4+ pXP2d2-rPAP1-luci+pUT651;
    (c)  pSV-SPORT-β$_c$/LepR-F3+pSV-SPORT-GM-CSFRα/ LepR-F3-Smad3+pMG2-Smad4+pXP2d2-rPAP1-luci+pUT651;
    (d)  pSV-SPORT-β$_c$/LepR-F3-Smad3+pSV-SPORT-GM-CSFRα/LepR-F3+pMG2-Smad4+pXP2d2-rPAP1-luci+pUT651;
    (e)    pSV-SPORT-β$_c$/LepR-F3-ALK4CA+pSV-SPORT-GM-CSFRα/LepR-F3+pMG2-Smad4+pXP2d2-rPAP1-luci+pUT651;
    (f)  pSV-SPORT-β$_c$/LepR-F3+pSV-SPORT-GM-CSFRα/ LepR-F3-ALK4CA+pMG2-Smad4+pXP2d2-rPAP1-luci+pUT651;
    (g)    pSV-SPORT-β$_c$/LepR-F3-ALK4CA+pSV-SPORT-GM-CSFRα/LepR-F3-Smad3+pMG2+pXP2d2-rPAP1-luci+pUT651;
    (h)  pSV-SPORT-β$_c$/LepR-F3-Smad3+pSV-SPORT-GM-CSFRα/LepR-F3-ALK4CA+pMG2+pXP2d2-rPAP1-luci+pUT651;
    (i)    pSV-SPORT-β$_c$/LepR-F3-ALK4CA+pSV-SPORT-GM-CSFRα/LepR-F3-Smad3+pMET7-Smad4+ pXP2d2-rPAP1-luci+pUT651; and
    (j)  pSV-SPORT-β$_c$/LepR-F3-Smad3+pSV-SPORT-GM-CSFRα/LepR-F3-ALK4CA+pMET7-Smad4+ pXP2d2-rPAP1-luci+pUT651.

A precipitation mixture of 300 µl was prepared which contained 2.92 µg (0.02 µg for pUT651, 0.2 µg for pXP2d2-rPAP1-luci+0.9 µg of each of the others). Two hundred µl of this mixture was applied to the cells. After 6 hours, the cells were washed once with Dulbecco's PBS and DMEM medium was added. After 48 hours, the cells were resuspended in 200 µl Cell Dissociation Agent. After neutralization with 2,200 µl DMEM medium, 40 µl of the cell suspension was placed into a 96-well plate (Costar). The cells were stimulated in a final volume of 100 µl with final concentrations of 1 ng/ml GM-CSF, 1 ng/ml GM-CSF plus 10 µM forskolin, 10 µM forskolin or were left unstimulated. Twenty-four hours after stimulation, luciferase and galactosidase activity assays were performed as described herein.

From these results (FIG. 11), it can be concluded that the cells from transfections c, d, e, f, g, h, i, and j showed no significant induction of luciferase activity. Cells from transfection a show a slight induction with GM-CSF (three-fold), which is increased to 37-fold when co-stimulated with forskolin. Transfection experiment b shows a clear induction of the rPAP1 promoter with GM-CSF (nine-fold), which is again more pronounced when co-stimulated with forskolin (71-fold). This indicates a bait-modifying enzyme activity ALK4CA-dependent phosphorylation of the Smad3 bait which results in an interaction between Smad4 and phosphorylated Smad3. The interaction leads to gp130 phosphorylation, STAT activation and signaling towards the rPAP1 promoter, thus leading to luciferase activity.

Example 9

The Use of MAPPIT to Screen Compound-Compound Interactions Comprising Non-Polypeptide Compounds An experiment is performed with Fujisporin, whereby FK506 is chemically linked to cyclosporin A (e.g., WO 94/18317). Alternatively, bivalent compounds are obtained by fusing FK506 to tetracycline or to a steroid ligand. Such hybrid compounds have the capacity to interact with the protein partners FKBP12 and cyclophilin (or tetracycline/steroid receptors).

Cells stably expressing the receptor/FKBP12 chimera are treated with the membrane-permeable divalent compound and after washing away excess compound, the cells are infected or transfected to enforce "prey" expression. Alternatively, both receptor/FKBP12 and "prey" chimeras are simultaneously expressed prior to addition of the compound. Careful compound dose-response experiments are performed and, given the dimerizer effect of the hybrid compounds, bell-shaped dose-response curves are obtained. The addition of excess monovalent compound is used as specificity control and reduces significantly signal output.

TABLE 1

Oligonucleotides used for construction of the described vectors:

| Number | Specification | Forward Reverse | Sequence (5'-3') |
|---|---|---|---|
| MBU-O-157 | Y985F mutagenesis in mLepR | F | GAGACAACCCTCAGTTAAATTTGC AACTCTGGTCAGCAACG (SEQ ID NO: 1) |
| MBU-O-158 | Y985F mutagenesis in mLepR | R | CGTTGCTGACCAGAGTTGCAAATT TAACTGAGGGTTGTCTC (SEQ ID NO: 2) |
| MBU-O-159 | Y1077F mutagenesis in mLepR | F | GGGAGAAGTCTGTCTGTTTTCTAG GGGTCACCTCCGTCAAC (SEQ ID NO: 3) |
| MBU-O-160 | Y1077F mutagenesis in mLepR | R | GTTGACGGAGGTGACCCCTAGAAA ACAGACAGACTTCTCCC (SEQ ID NO: 4) |
| MBU-O-161 | Y1138F mutagenesis in mLepR | F | CTGGTGAGAACTTTGTACCTTTTAT GCCCCAATTTCAAACCTG (SEQ ID NO: 5) |
| MBU-O-162 | Y1138F mutagenesis in mLepR | R | CAGGTTTGAAATTGGGGCATAAAA GGTACAAAGTTCTCACCAG (SEQ ID NO: 6) |
| MBU-O-167 | hEpoR primer | F | CGGGGTACCATGGACCACCTCGGG GCGTCC (SEQ ID NO: 7) |
| MBU-O-222 | rPAP1 promoter primer | F | CTGCAGATTTTCCAGTTAGTCA (SEQ ID NO: 8) |
| MBU-O-223 | rPAP1 promoter primer | R | TGGATGGTTTGTGAGGACAG (SEQ ID NO: 9) |
| MBU-O-308 | hEpoR primer | R | CCCTTAATTAAGTCCAGGTCGCTA GGCGTCAG (SEQ ID NO: 10) |
| MBU-O-443 | hgp130 primer | R | GCGAATTCCGAACCGCCCTGAGGC ATGTAGCCGCC (SEQ ID NO: 11) |
| MBU-O-445 | SV40 LargeT primer | F | GCGAATTCGAAGCAGAGGAAACT AAACAAGTG (SEQ ID NO: 12) |
| MBU-O-446 | SV40 LargeT primer | R | CGTCTAGAGCGGCCGCAGATCTCG AGTCGCGATTATGTTTCAGGTTCA GGGGGAG (SEQ ID NO: 13) |
| MBU-O-447 | mLepR intracellular and transmembrane fragment | F | GCTTAATTAACGGGCTGTATGTCA TTGTACC (SEQ ID NO: 14) |

TABLE 1-continued

Oligonucleotides used for construction of the described vectors:

| Number | Specification | Forward Reverse | Sequence (5'-3') |
|---|---|---|---|
| MBU-O-448 | mLepR intracellular and transmembrane fragment | R | CGTCTAGATTAGCGGCCGCTTACT AGTGAGCTCGTCGACCCACCCACA GTTAAGTCACACATC (SEQ ID NO: 15) |
| MBU-O-450 | mp53 primer | F | GTGTCGACGGTCACCGAGACCCCT GGG (SEQ ID NO: 16) |
| MBU-O-451 | mp53 primer | R | GCTCTAGATCATTGCGGGGGAGAG GCGC (SEQ ID NO: 17) |
| MBU-O-467 | hGRB2 primer | F | GGAATTCATGGAAGCCATCGCCAA ATA (SEQ ID NO: 18) |
| MBU-O-468 | hGRB2 primer | R | GCTCTAGATTAGACGTTCCGGTTC ACGG (SEQ ID NO: 19) |
| MBU-O-469 | hGRB2 SH2 primer | F | GGAATTCTGGTTTTTTGGCAAAAT CCC (SEQ ID NO: 20) |
| MBU-O-470 | hGRB2 SH2 primer | R | GCTCTAGATTACGGCTGCTGTGGC ACCT (SEQ ID NO: 21) |
| MBU-O-515 | Mutagenesis IRS1 primer | F | GGTGAGAACTTTGTAAGCCCGGGT GAATATGTCAATATTGAATTCCAA TTTCAAACCTG (SEQ ID NO: 22) |
| MBU-O-516 | Mutagenesis IRS1 primer | R | CAGGTTTGAAATTGGAATTCAATA TTGACATATTCACCCGGGCTTACA AAGTTCTCACC (SEQ ID NO: 23) |
| MBU-O-567 | Mutagenesis ApaI site primer | F | GCTCTAAAAGCTCCGGGCCCAGTA GGAATTCTAATACG (SEQ ID NO: 24) |
| MBU-O-568 | Mutagenesis ApaI site primer | R | CGTATTAGAATTCCTACTGGGCCC GCAGCTTTTAGAGC (SEQ ID NO: 25) |
| MBU-O-586 | hgp130 primer | F | GACGGGCCCGCCACCATGGATTAC AAGGATGACGACGATAAGATCTCG ACCGTGGTACACAGTGGC (SEQ ID NO: 53) |
| MBU-O-675 | hEpoR intr. fragment primer | F | GGCGAGCTCGGTGCTGGACAAATG GTTGC (SEQ ID NO: 27) |
| MBU-O-676 | hEpoR intr. fragment primer | R | CGCTCTAGATTACTTTAGGTGGGG TGGGGTAG (SEQ ID NO: 28) |
| MBU-O-677 | mCIS primer | F | GCGGAATTCGTCCTCTGCGTACAG GGATC (SEQ ID NO: 29) |
| MBU-O-678 | mCIS primer | R | GCCTCTAGATCAGAGTTGGAAGGG GTACTG (SEQ ID NO: 30) |
| MBU-O-695 | SV40 LargeT primer | F | GCGAGATCTCGGAAGCAGAGGAA ACTAAACAACTG (SEQ ID NO: 31) |

TABLE 1-continued

Oligonucleotides used for construction of the described vectors:

| Number | Specification | Forward Reverse | Sequence (5'-3') |
|---|---|---|---|
| MBU-O-696 | SV40 LargeT primer | R | GCGTCTAGATTATGTTTCAGGTTCA GGGGGAG (SEQ ID NO: 32) |
| MBU-O-717 | hEpoR Y426-F mutagenesis | F | CTGCCAGCTTTGAATTCACTATCCT GGAC (SEQ ID NO: 33) |
| MBU-O-718 | hEpoR Y426-F mutagenesis | R | GTCCAGGATAGTGAATTCAAAGCT GGCAG (SEQ ID NO: 34) |
| MBU-O-719 | Puro$^R$ primer | F | CCGCTCGAGCCACCATGGCCGAGT ACAAGCCCACG (SEQ ID NO: 40) |
| MBU-O-720 | Puro$^R$ primer | R | GCTCTAGATTAGGCACCGGGCTTG CGG (SEQ ID NO: 41) |
| MBU-O-737 | hVavS primer | F | GCGGAATTCAAGCTGGAGGAATGT TCTCA (SEQ ID NO: 35) |
| MBU-O-738 | hVavS primer | R | CGCCTCGAGTTACACGTAGTTGGC AGGGAACC (SEQ ID NO: 36) |
| MBU-O-741 | hVavS primer | R | CGCTCTAGATTACACGTAGTTGGC AGGGAACC (SEQ ID NO: 37) |
| MBU-O-766 | gp130 primer | F | GCGGGATCCGCCACCATGGATTAC AAG (SEQ ID NO: 42) |
| MBU-O-769 | hEpoR primer | R | GCGCGGCCGCTTACTTTAGGTGGG GTGGGGTAG (SEQ ID NO: 43) |
| MBU-O-770 | hGRB2 SH3 primer | F | GCGAGATCTCGACATACGTCCAGG CCCTCTTTGAC (SEQ ID NO: 38) |
| MBU-O-771 | hVAVS primer | F | GCGGGATCCCGAAGCTGGAGGAAT GTTCTCA (SEQ ID NO: 39) |
| MBU-O-835 | ccdB primer | F | CGGAATTCGCTTACTAAAAGCCAG (SEQ ID NO: 44) |
| MBU-O-836 | ccdB primer | R | ATAGTTTAGCGGCCGCTAATTCTA TATTCCCC (SEQ ID NO: 45) |
| MBU-O-1094 | Gateway-primer | F | GGGGACAAGTTTGTACAAAAAAGC AGGCTACTTACCACAGACTGTACG (SEQ ID NO: 46) |
| MBU-O-1076 | Gateway-primer | R | CCCCACCACTTTGTACAAGAAAGC TGGGTCTGCATTCATTTTATGTTTCA (SEQ ID NO: 47) |

REFERENCES

Eyckerman S., W. Waelput, A. Verhee, D. Broekaert, J. Vandekerckhove, and J. Tavernier (1999). Analysis of Tyr to Phe and fa/fa leptin receptor mutations in the PC12 cell line. *Eur. Cytokine Netw.* 10:549-556.

Fields S. and O. K. Song (1989). A novel genetic system to detect protein-protein interactions. *Nature* 340:245-246.

Fisher M., J. Goldschmitt, C. Peschel, K. J. Kallen, J. P. J. Brakenhoff, A. Wollmer, J. Grotzinger, and S. Rose-John (1997). A designer cytokine with high activity on human hemapoietic progenitor cells. *Nat. Biotechnol.* 15:142-145.

Graham F. L. and A. J. van der Eb (1973). Transformation of rat cells by DNA of human adenovirus 5. *Virology* 54:536-539.

Pattyn E., X. Van Ostade, L. Schauvliege, A. Verhee, M. Kalai, J. Vandekerckhove, and J. Tavernier (1999). Dimerization of the interferon type I receptor IFNaR2-2 is sufficient for induction of interferon effector genes but not for full antiviral activity. *J. Biol. Chem.* 274:34838-34845.

Kitamura T., M. Onishi, S. Kinoshita, A. Shibuya, A. Miyajima, and G. P. Nolan (1995). Efficient screening of retroviral cDNA expression libraries. *Proc. Natl. Acad. Sci. USA* 14:9146-9150.

Kojima T and T. Kitamura (1999). A signal sequence trap based on a constitutively active cytokine receptor. *Nat. Biotechnol.* 17:487-490.

Takebe Y., M. Seiki, J. Fujisawa, P. Hoy, K. Yokota, K. Arai, M. Yoshida, and N. Arai (1988). SR alph promoter: an efficient and versatile mammalian cDNA expression system composed of the simian virus 40 early promoter and the R-U5 segment of human T-cell leukemia virus type 1 log terminal repeat. *Mol. Cell. Biol.* 8:466-472.

Wiley J. C., L. A. Wailes, R. L. Idzerda, and G. S. McKnight (1999). Role of regulatory subunits and protein kinase inhibitor (PKI) in determining nuclear localization and activity of the catalytic subunit of protein kinase A. *J. Biol. Chem.* 274:6381-6387.

What is claimed is:

1. A receptor complex comprising:

a recombinant receptor polypeptide comprising an extracellular ligand-binding domain derived from a receptor; and a cytoplasmic domain derived from a receptor, wherein at least one activation site of the cytoplasmic domain has been inactivated by either mutation, deletion, or mutation and deletion, the cytoplasmic domain comprising at least two parts:

a first part derived from a cytoplasmic domain of a receptor; and a second part comprising a heterologous bait polypeptide which is heterologous to the cytoplasmic domain of the receptor from which the first part is derived;

wherein the cytoplasmic domain comprises at least a JAK binding site; and a recombinant prey polypeptide comprising a first polypeptide that interacts with the heterologous bait polypeptide and a second polypeptide comprising at least one activation site;

wherein the receptor complex is activated by binding of a ligand to the extracellular ligand-binding domain and by binding of the recombinant prey polypeptide to the heterologous bait polypeptide.

2. The receptor complex of claim 1, wherein the recombinant receptor polypeptide is a homomultimerizing receptor polypeptide.

3. The receptor complex of claim 1, wherein the recombinant receptor polypeptide is a heteromultimerizing receptor polypeptide.

4. A eukaryotic cell comprising the receptor complex of claim 1.

5. The eukaryotic cell of claim 4, wherein the eukaryotic cell is selected from the group consisting of a mammalian cell, a fungal cell, and a plant cell.

* * * * *